(12) United States Patent
Liu et al.

(10) Patent No.: US 11,980,583 B2
(45) Date of Patent: May 14, 2024

(54) SYSTEM, APPARATUS, AND METHOD FOR CONTROLLING DEVICES BASED ON ACCUMULATION OF INPUT

(71) Applicant: HYTTO PTE. LTD, Singapore (SG)

(72) Inventors: Dan Liu, Guangdong (CN); Jilin Qiu, Guangdong (CN)

(73) Assignee: HYTTO PTE. LTD., Singapore (SG)

( * ) Notice: Subject to any disclaimer, the term of this patent is extended or adjusted under 35 U.S.C. 154(b) by 0 days.

(21) Appl. No.: 18/188,838

(22) Filed: Mar. 23, 2023

(65) Prior Publication Data

US 2023/0225931 A1    Jul. 20, 2023

Related U.S. Application Data

(63) Continuation of application No. 17/835,265, filed on Jun. 8, 2022, now Pat. No. 11,642,276, which is a continuation-in-part of application No. 17/722,540, filed on Apr. 18, 2022, which is a continuation-in-part of application No. 17/671,783, filed on Feb. 15, 2022, said application No. 17/835,265 is a continuation-in-part of application No. 17/717,917, filed on Apr. 11, 2022, which is a continuation of application No. 16/352,876, filed on Mar. 14, 2019, now Pat. No. 11,311,453, said application No. 17/835,265 is a continuation-in-part of application No. 16/835,808, filed on Mar. 31, 2020, now Pat. No. 11,452,669.

(Continued)

(51) Int. Cl.
*A61H 19/00* (2006.01)
*A61F 5/41* (2006.01)
*A61H 23/02* (2006.01)

(52) U.S. Cl.
CPC ............... *A61H 19/44* (2013.01); *A61F 5/41* (2013.01); *A61H 19/34* (2013.01); *A61F 2005/417* (2013.01); *A61H 23/02* (2013.01); *A61H 2201/5007* (2013.01); *A61H 2201/5071* (2013.01); *A61H 2201/5097* (2013.01)

(58) Field of Classification Search
None
See application file for complete search history.

(56) References Cited

U.S. PATENT DOCUMENTS 3,361,130 A    1/1968 Vernon
5,807,287 A    9/1998 Cheng
(Continued)

FOREIGN PATENT DOCUMENTS

KR    101256565 B1    4/2013
WO    2006040750 A1    4/2006
WO    2008067487 A2    6/2008

*Primary Examiner* — Christine H Matthews
(74) *Attorney, Agent, or Firm* — Holtz, Holtz & Volek PC

(57) ABSTRACT

An adult toy is configured to communicate with a user device of a human user. Receipt of a plurality of input parameters is accumulated via the user device. In response to the accumulation satisfying a preset condition, the accumulation is stopped and a control signal is sent to actuate the adult toy to perform a series of predefined acts. The series of predefined acts are used to sexually stimulate the human user. The control signal includes one or more control sub-patterns, each of the one or more control sub-patterns being configured by each of the plurality of input parameters.

16 Claims, 21 Drawing Sheets

Related U.S. Application Data

(60) Provisional application No. 62/830,195, filed on Apr. 5, 2019.

(56) References Cited

U.S. PATENT DOCUMENTS

| | | |
|---|---|---|
| 6,277,085 B1 | 8/2001 | Flynn |
| 6,368,268 B1 | 4/2002 | Sandvick et al. |
| 8,255,299 B2 | 8/2012 | Cambridge |
| 8,644,967 B2 | 2/2014 | Seiler |
| 8,936,544 B2 | 1/2015 | Shahoian et al. |
| 9,762,515 B1 | 9/2017 | Olivares et al. |
| 10,051,328 B2 | 8/2018 | Olivares et al. |
| 10,218,795 B1 | 2/2019 | Messinger |
| 10,576,013 B1 | 3/2020 | Sloan |
| 11,134,041 B1 | 9/2021 | He |
| 11,642,276 B2 * | 5/2023 | Liu ................. A63F 13/28 600/38 |
| 2002/0065477 A1 | 5/2002 | Boyd et al. |
| 2002/0133103 A1 | 9/2002 | Williams et al. |
| 2003/0036678 A1 | 2/2003 | Abbassi |
| 2004/0082831 A1 | 4/2004 | Kobashikawa et al. |
| 2004/0097852 A1 | 5/2004 | Boyd et al. |
| 2005/0138560 A1 | 6/2005 | Lee et al. |
| 2006/0247561 A1 | 11/2006 | Chiu |
| 2011/0133910 A1 | 6/2011 | Alarcon |
| 2012/0259171 A1 | 10/2012 | Shmakov |
| 2012/0304216 A1 | 11/2012 | Strong |
| 2013/0165747 A1 | 6/2013 | Maggs |
| 2014/0011557 A1 | 1/2014 | Coyle |
| 2014/0115690 A1 | 4/2014 | Huang et al. |
| 2016/0049043 A1 | 2/2016 | Tennenhaus et al. |
| 2016/0199249 A1 | 7/2016 | Dunham et al. |
| 2017/0119619 A1 | 5/2017 | Dills |
| 2018/0116904 A1 | 5/2018 | Lieberman et al. |
| 2019/0133877 A1 | 5/2019 | Cambridge |
| 2020/0009009 A1 | 1/2020 | Nishida |
| 2020/0276504 A1 | 9/2020 | Liu |
| 2020/0289363 A1 | 9/2020 | Liu |
| 2020/0315908 A1 | 10/2020 | Liu |
| 2020/0366972 A1 | 11/2020 | Sloan |
| 2021/0341992 A1 | 11/2021 | Cambridge |
| 2022/0141550 A1 | 5/2022 | Liu |

* cited by examiner

| | |
|---|---|
| RECEIVE, BY A PROCESSOR, A MEDIA SELECTION REQUEST INITIATED FROM A USER INTERFACE (UI) OF A MEDIA APPLICATION INSTALLED ON A USER DEVICE COMMUNICABLY CONNECTED TO AN ADULT ENTERTAINMENT DEVICE, WHEREIN THE MEDIA SELECTION REQUEST COMPRISES A SELECTED MEDIA FILE, AND WHEREIN THE MEDIA APPLICATION IS FACILITATED BY A SERVER SYSTEM | 1002 |
| DETECT, BY THE PROCESSOR, AT LEAST ONE SCRIPT FILE OF A PLURALITY OF SCRIPT FILES CORRESPONDING TO THE SELECTED MEDIA FILE ON THE USER DEVICE AND ON THE SERVER SYSTEM | 1004 |
| DISPLAY, BY THE PROCESSOR, A LIST OF LOCAL SCRIPT FILES DETECTED FROM THE USER DEVICE AND A LIST OF PUBLIC SCRIPT FILES DETECTED FROM THE SERVER SYSTEM | 1006 |
| RECEIVE, BY THE PROCESSOR, A USER SELECTION OF A SCRIPT FILE FROM ONE OF THE LIST OF LOCAL SCRIPT FILES AND THE LIST OF PUBLIC SCRIPT FILES, WHEREIN THE SELECTED SCRIPT FILE COMPRISES A CORRESPONDING PATTERN CREATED FOR THE SELECTED MEDIA FILE | 1008 |
| PLAY, BY THE PROCESSOR, THE SELECTED MEDIA FILE ASSOCIATED WITH THE SELECTED SCRIPT FILE | 1010 |
| SEND, BY THE PROCESSOR, ONE OR MORE INTENSITY INSTRUCTION SIGNALS TRANSFORMED FROM THE PATTERN IN THE SELECTED SCRIPT FILE TO THE ADULT ENTERTAINMENT DEVICE, WHEREIN RECEIPT OF THE ONE OR MORE INTENSITY INSTRUCTION SIGNALS CAUSES THE ADULT ENTERTAINMENT DEVICE TO PERFORM CUSTOMIZATION OF ONE OR MORE ADJUSTABLE PARAMETERS OF THE ADULT ENTERTAINMENT DEVICE TO BE IN SYNCHRONIZATION WITH THE PLAYED MEDIA FILE ASSOCIATED WITH THE SELECTED SCRIPT FILE | 1012 |

EXEMPLARY IMPLEMENTATION

```
const onMouseMoveEvent = throttle(function(ev) {
    if(editorMode.edMode === 1 && isMouseDown){
    // Calculate the distance of the mouse sliding from click events
        let moveDistance = mouseDownY - ev.clientY + oldBottom;
        if(moveDistance >= -X && moveDistance <= Y){
            let bottom = parseInt(Math.floor((moveDistance - min)/lvHeight)*lvHeight + min);
            if(bottom >= min && bottom <= max){
                setConBoxBottom(bottom);
            }
            if(bottom < min){
                bottom = min;
            }else if(bottom > max){
                bottom = max;
            }
        // Convert mouse sliding into vibration intensity
        let levelTmp = orderUtil.getLevel(bottom, min, max);
        if(levelRange && levelTmp > levelRange.max){
            levelTmp = levelRange.max;
        }else if(levelRange && levelTmp < levelRange.min){
            levelTmp = levelRange.min;
        }
        setLevel(levelTmp);
        if (!timer) {
            if(videoPlaying && editorMode.edMode === 1){
                let tmpPointsArr = orderUtil.deepClone(points);
                let currentTimePoint = tmpPointsArr.find(i => i.t === progress);
                if(currentTimePoint) {
                    // currentTimePoint.v = levelTmp;
                    // setPoints(tmpPointsArr);
                } else {
                    let curTime = orderUtil.formatMs(parseInt(videoEl.currentTime*1000));
                    if(tmpPointsArr.length > 0){
                        let prevTime = curTime - tmpPointsArr[tmpPointsArr.length - 1].t;
                        ......
    return false;
    }
```

*Fig. 13*

SYSTEM, APPARATUS, AND METHOD FOR CONTROLLING DEVICES BASED ON ACCUMULATION OF INPUT

CROSS REFERENCE TO RELATED APPLICATIONS

This application is a continuation of U.S. patent application Ser. No. 17/835,265, filed Jun. 8, 2022, which is a continuation-in-part of U.S. patent application Ser. No. 17/722,540, filed Apr. 18, 2022, which is a continuation-in-part of U.S. patent application Ser. No. 17/671,783, filed Feb. 15, 2022. Parent U.S. patent application Ser. No. 17/835,265, filed Jun. 8, 2022, is also a continuation-in-part of U.S. patent application Ser. No. 17/717,917, filed Apr. 11, 2022, which is a continuation of U.S. patent application Ser. No. 16/352,876, filed Mar. 14, 2019 (now U.S. Pat. No. 11,311,453 issued on Apr. 26, 2022). Parent U.S. patent application Ser. No. 17/835,265, filed Jun. 8, 2022, is also a continuation-in-part of U.S. patent application Ser. No. 16/835,808, filed Mar. 31, 2020 (now U.S. Pat. No. 11,452,669 issued on Sep. 27, 2022), which claims priority to U.S. Provisional Patent Application No. 62/830,195, filed Apr. 5, 2019. Each of the above applications is hereby incorporated by reference in its entirety.

FIELD OF THE INVENTION

The present disclosure generally relates to a system, apparatus, and method for controlling devices, and more particularly to a system, apparatus, and method for controlling devices based on accumulation of input.

BACKGROUND OF THE INVENTION

Sexual stimulation can be achieved by an individual or a group of individuals (irrespective of gender) by using adult toys. The adult toys can have a vibration feature for providing sexual stimulation. In conventional adult toys, a degree or intensity of sexual stimulation may be manually controlled. For example, the adult toys may be configured with an on/off switch. However, as these conventional adult toys are typically self-operated by the individual for experiencing sexual stimulation by using a single setting in the adult toy, the individual may not always feel the same level of stimulation at every instance using the adult toy. Additionally, the arousal of the individual may change periodically based on mood and environment, and thus the stimulation produced by the adult toy using a single vibration setting may not satisfy the individual.

Currently, social media and the ability to extend wireless interfaces, local and wide area networking etc., have contributed to the configurability of adult toys. These technologies provide a level of customization to the needs of the individual or the group of individuals to experience sexual stimulation without direct physical contact. However, these technologies do not provide for control of adult toys based on tipping patterns.

The exemplary disclosed system, apparatus, and method are directed to overcoming one or more of the shortcomings set forth above and/or other deficiencies in existing technology.

SUMMARY OF THE INVENTION

In one exemplary aspect, the present disclosure is directed to a system. The system includes an accessory control module, comprising computer-executable code stored in non-volatile memory, a memory for storing instructions and a processor for executing the instructions, a user device of a user, and an accessory configured to communicate with the user device. The accessory control module, the memory and the processor, the user device, and the accessory are configured to accumulate receipt of one or more input parameters, determine whether an accumulation satisfies a preset condition, wherein the preset condition includes at least one of a preset receiving quantity of the one or more input parameters, a preset receiving sum of values of the one or more input parameters, or a preset time duration of the accumulation, and in response to the accumulation satisfying the preset condition, send a control signal to actuate the accessory to perform a series of predefined acts, wherein the series of predefined acts is configured to sexually stimulate the user.

In another aspect, the present disclosure is directed to a method. The method includes providing a user device of a human user, providing an adult toy configured to communicate with the user device, accumulating receipt of a plurality of input parameters via the user device, determining whether an accumulation satisfies a preset condition, wherein the preset condition includes at least one of a preset receiving quantity of the plurality of input parameters, a preset receiving sum of values of the plurality of input parameters, or a preset time duration of the accumulation, and in response to the accumulation satisfying the preset condition, sending a control signal to actuate the adult toy to perform a series of predefined acts, wherein the series of predefined acts is configured to sexually stimulate the human user.

BRIEF DESCRIPTION OF THE DRAWINGS

For a more complete understanding of example embodiments of the present technology, reference is now made to the following descriptions taken in connection with the accompanying drawings in which:

FIG. 10 is a flowchart illustrating another method for playing at least one pattern of the multimedia file while using the adult entertainment device, in accordance with an example embodiment of the present disclosure;

FIG. 13 is an exemplary implementation, in accordance with an example embodiment of the present disclosure.

Figure 1:
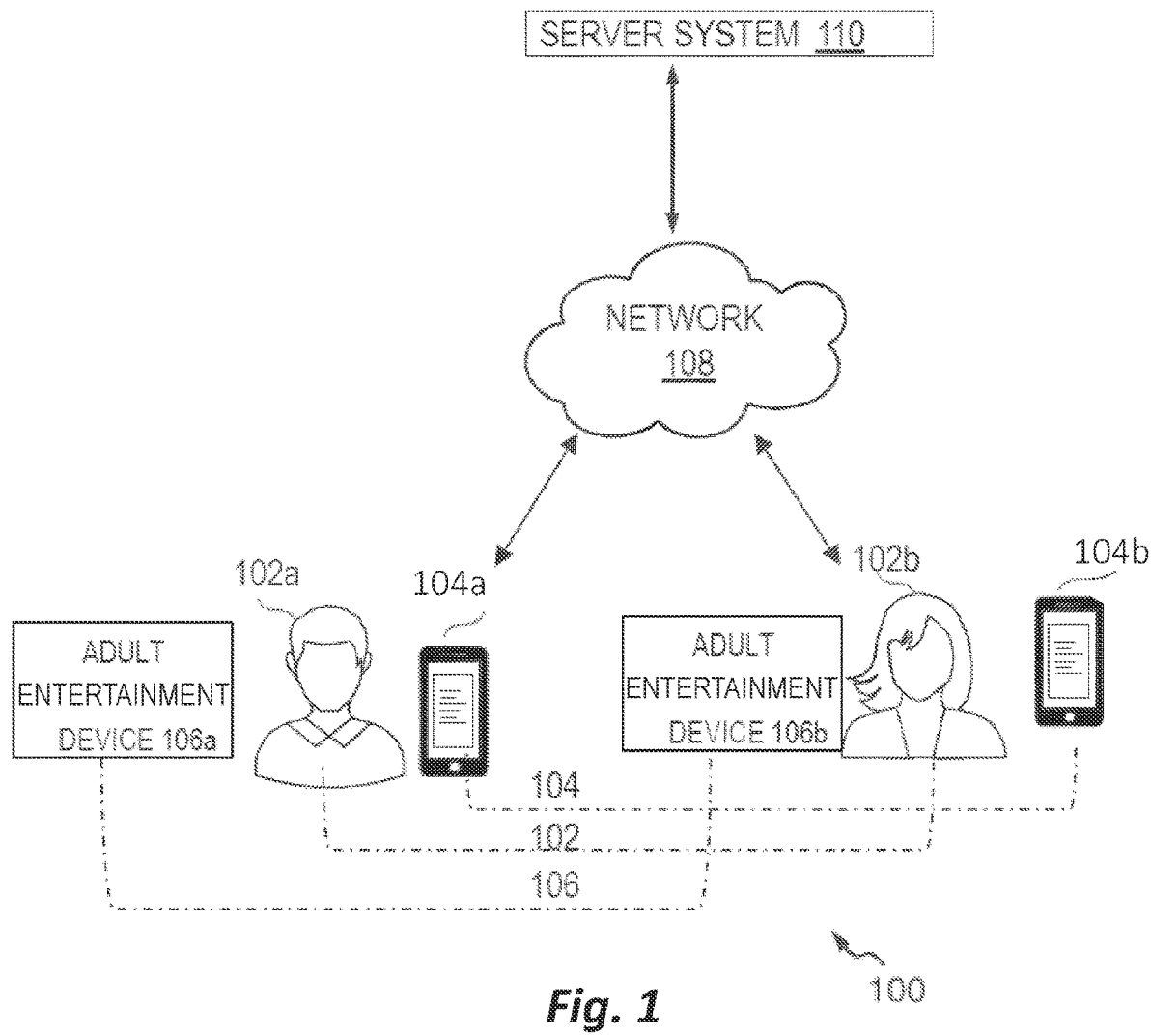
FIG. 1 is an illustration of an environment, where at least some example embodiments can be practiced.

The drawings referred to in this description are not to be understood as being drawn to scale except if specifically noted, and such drawings are only exemplary in nature.

DETAILED DESCRIPTION AND INDUSTRIAL APPLICABILITY

In at least some exemplary embodiments, the exemplary disclosed system, apparatus, and method may include systems and methods for operating adult entertainment devices or stimulation equipment in synchronization with a multimedia file. The exemplary disclosed system, apparatus, and method may provide methods and systems for creating patterns for an adult entertainment device.

In at least some exemplary embodiments, the exemplary disclosed system, apparatus, and method may provide methods and systems for creating patterns for an adult entertainment device. The exemplary disclosed system, apparatus, and method may include a software platform incorporated with a server system, that may be provided for facilitating the creation of at least one control pattern for a multimedia file while playing the multimedia file. A user may access a multimedia file by selecting the multimedia file over a network or by uploading a multimedia file to the user device for which the user wants to create a pattern. A user may also open a local multimedia file for example as described below. The server system may be communicably coupled to the user's device and an adult entertainment device. The creation of a control pattern for the multimedia file may cause customization of a series of predefined acts of the adult entertainment device for performing at least one predefined act at different amplitudes in synchronization with the selected multimedia file.

In at least some exemplary embodiments, a user may access a multimedia file by opening a local multimedia file that may be stored locally. For example, the multimedia file may be stored locally on storage media of the exemplary disclosed user device. In at least some exemplary embodiments, the local multimedia file may be opened using a multimedia player that may be operated by the user using the exemplary disclosed user device.

In at least some exemplary embodiments, the exemplary disclosed system, apparatus, and method may facilitate pattern creation, the server system may play the multimedia file uploaded and/or selected by the user based on a multimedia play request received from the user device for playing the multimedia file. The server system may then provide a plurality of pattern creation options on a UI while playing the multimedia file. The user may use a pattern creation set option of the plurality of pattern creation options that may be provided on the UI for creating the control pattern for the multimedia file being played.

The control pattern (e.g., control pattern creation options) may then be stored in a corresponding script file that may be stored either on the server system associated with the multimedia application or on the user device or integrated into the browser application or integrated into the live streaming application. For example, the exemplary disclosed system, apparatus, and method may include a UI operable interface including various pattern creation options, which may be stored in a corresponding script file (e.g., JS script file). Based on calling the script file, the exemplary disclosed UI operable interface may be displayed at or near (e.g., next to) a multimedia playback window. For example, a script may be shown and indicated as integrated with multimedia such as video files. A user may utilize an editing operation of the exemplary disclosed UI operable interface to create the exemplary disclosed control patterns. In at least some exemplary embodiments, the exemplary disclosed UI operable interface may include a set of software development tools (e.g., one or more software development kits) that may be utilized by users to create the exemplary disclosed control patterns. For example, software development kits may be provided via online audio and/or video platforms for use with the exemplary disclosed UI operable interface.

The server system may provide various options to edit, save, share and forward the created control pattern set. The created pattern may include at least one input signal set that actuates the adult entertainment device to customize successive predefined acts to sequentially perform at least one predefined act as a series at different amplitudes. The predefined act can include one or more combinations of vibration, rotation, swinging, inhalation, temperature variation, expansion, suction, and contraction.

For viewing a specific control pattern from a plurality of control patterns of the multimedia file, the user may select the media file and a plurality of script files associated with the corresponding to the pattern sets that are created for the media file. One or more of the files may be displayed on the UI of the media application. The user may now select a script file that the user wants to play, and the media file associated with the selected script file may then be played on the user device.

The server system may then send one or more intensity instruction signal sets to be transformed from a corresponding control pattern present in the selected script file to the adult entertainment device connected to the user device. The adult entertainment device, upon receiving the intensity instruction signals set, causes to synchronize one or more created control patterns into the multimedia file being played, to sequentially perform a successive series of pre-defined acts with different amplitudes. The synchronization of the one or more created control patterns with the played multimedia file may provide for the movements of a character in the played multimedia file being synced with the operation of the adult entertainment device, thereby providing a real-time pleasurable engagement to the user using the adult entertainment device.

In the following description, numerous specific details are set forth in order to provide a thorough understanding of the present disclosure. It will be apparent, however, to one skilled in the art that the present disclosure can be practiced without these specific details. In other instances, systems and methods are shown in block diagram form in order to avoid obscuring the present disclosure.

Reference in this specification to "one embodiment" or "an embodiment" means that a particular feature, structure, or characteristic described in connection with the embodiment is included in at least one embodiment of the present disclosure. The appearance of the phrase "in one embodiment" in various places in the specification is not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

Various example embodiments of present disclosure are described hereinafter with reference to FIGS. 1 to 12.

FIG. 1 is an illustration of an environment 100 related to at least some example embodiments of the present disclosure. The environment 100 includes, but is not limited to, a wireless communication network (e.g., a network 108) that connects entities such as users 102a and 102b, and a server system 110. The users 102a and 102b are depicted to be associated with electronic devices 104a and 104b (hereinafter referred to as 'user device 104a, and user device 104b', respectively) and adult entertainment devices 106a and 106b, respectively. It should be noted that each user is shown to be associated with a single adult entertainment device for the sake of simplicity, but each user can be associated with multiple adult entertainment devices. It should be noted that the users 102a and 102b are collectively referred to as a user 102, the user devices 104a and 104b are collectively referred to as a user device 104 and the adult entertainment devices 106a and 106c are collectively referred to as an adult entertainment device 106.

In an embodiment, the user device 104 may be equipped with a server system 110 that facilitates the creation of control patterns for at least one predefined act with a series of different amplitude for a multimedia file. The user device 104 may be any communication device having hardware components for enabling User Interfaces (UIs) of the server system 110 to be presented on the user device 104. The user device 104 may be capable of being connected to a wireless communication network (such as the network 108). Examples of the user device 104 include a mobile phone, a smart telephone, a computer, a laptop, a PDA (Personal Digital Assistant), a Mobile Internet Device (MID), a tablet computer, an Ultra-Mobile personal computer (UMPC), a phablet computer, a handheld personal computer and the like.

Examples of the network 108 include stand-alone or a combination of a local area network (LAN), a wide area network (WAN), wireless, wired, any currently existing or to be developed network that can be used for communication. More specifically, an example of the network 108 can be the Internet which may be a combination of a plurality of networks.

In at least one example embodiment, the server system 110 is configured to electronically connect the user device 104 with the adult entertainment device 106 using any wired or wireless technologies. In an embodiment, the server system 110 electronically connects the user device 104 with the adult entertainment device 106 using Bluetooth technology. The user device 104 and the adult entertainment device 106 may be Bluetooth-enabled devices for supporting connection establishment using the Bluetooth technology.

In some embodiments, the server system 110 may provide an application that facilitates the creation of control pattern sets of a predefined act for the multimedia file, in response to a request received from the user device 104 via the network 108. Further, it is noted that the application may be present on the server system 110 or the user device 104 or any other electronic device communicably coupled to the user device 104.

In an embodiment, the application may be factory-installed on the user device 104 and the user 102 may not specifically request the application from the server system 110. In another embodiment, the user device 104 may access an instance of the application from the server system 110 for installing on the user device 104 by accessing a media application domain. In yet another embodiment, the application may be accessed by the user device 104 through the web via the network 108. More specifically, the application may be accessed by the user device 104 through the web via the Internet.

In an embodiment, the server system 110 may be configured to facilitate uploading and/or selecting and playing of a multimedia file. The server system 110 may also be configured to facilitate the creation of a plurality of patterns as a control pattern set of a predefined act for the selected multimedia file. In one embodiment, the user 102 can create or edit a control pattern while playing the multimedia file. In another embodiment, the user 102 can create or edit a control pattern without playing the multimedia file. Examples of the multimedia file include, but is not limited to, a video file, an audio file, a text file, an image file and the like. The server system 110 is then configured to store each pattern of the plurality of patterns that may be created as at least one control pattern set for the media file in a corresponding script file. Additionally, the server system 110 may be configured to provide the features to save, share, download and edit (such as copy, cut, paste) for each control pattern that is created for the multimedia file by the user 102.

Further, the server system 110 may also be configured to detect and display the plurality of script files available corresponding to the plurality of patterns that are created as a set of control pattern for a predefined act and are available for each media file of the plurality of media files available in the user device 104. The server system 110 may then be configured to facilitate selection of a script file from the plurality of script files by the user 102. Further, the server system 110 may be configured to play the media file associated with the selected script file and create at least one intensity instructions set, wherein the intensity instructions set includes a plurality of intensity instruction signals by transforming the control pattern to sequentially perform at least one predefined act or a series of predefined acts at different amplitudes present in the selected script file of the adult entertainment device 106 in synchronization with the multimedia file being played.

Additionally, the server system 110 may be configured to send the one or more intensity instruction signals to the adult entertainment device 106 connected with the user device 104 along with the playing of the media file. In one embodiment, the played multimedia file can be recorded or stored file. In another embodiment, the played multimedia file is a live broadcast. In one embodiment, the one or more intensity instruction signals include at least one amplitude intensity instruction signal that may be created from the amplitude pattern included in the selected script. The at least one intensity instruction signal set is responsible for causing customization of at least one of a vibration, rotation, swing, temperature, expansion, suction, inhalation, and contraction of the adult entertainment device 106.

Further, the server system 110 during the reproduction or playback of the multimedia file with the created control patterns may be configured to generate a tipping request. The server system may generate the tipping request by defining tipping parameters to perform predefined acts, via the adult entertainment device 106, based on the number of tips received by the server system 110. The server system 110 may define the tip parameters. The tip parameters may include one or more ranges of tip amounts and the control patterns of the predefined act correlating to each of the one or more ranges. The server system 110 may display the tipping request on the user device 104 and in response may receive a tip from the user 102 through the tipping option displayed on the UI of the user device 104 (e.g., the tip may include virtual currency). The server system 110 may then determine whether the tip falls within the one or more ranges of the selected control pattern associated with the multimedia file. If the tip falls within the tip parameters of the control pattern with the predefined acts, the sever system may actuate the adult entertainment device 106 to perform at least one predefined act depending on an amount of the tip to stimulate the adult entertainment device 106.

In an embodiment, the adult entertainment device 106 can be a female entertainment device or a male entertainment device. The female entertainment device may be configured to stimulate pleasure hotspots in a body of a female by generating rotating and vibrating sensations at the pleasure hotspots. The male entertainment device may be configured to generate air pressure and vibrations around an intromittent organ of a male that creates a suction feeling in the intromittent organ that further helps in achieving masturbation.

Further, based on the receipt of the intensity instruction signals from the server system 110, the adult entertainment device 106 may be configured to perform customization of at least one predefined act of the adult entertainment device 106. The predefined act may include vibration, rotation, swing, temperature, expansion, suction, inhalation, and contraction of the adult entertainment device 106 to be in synchronization with the selected media file associated with the selected script file, which may enhance the sexual experience of the user 102 using the adult entertainment device 106. The working of the adult entertainment device 106 is further explained in detail with reference to FIG. 6.

In an example scenario, as shown in FIG. 1, the user 102 may want to create a pattern for a media file (e.g., XYZ.MPEG). The user 102 may use an application installed on the user device 104 communicatively coupled to the server system 110 for uploading or selecting the media file XYZ.MPEG. The media file XYZ.MPEG can be uploaded from a local drive on the user device 104 or the user 102 may upload the media file XYZ.MPEG to the server system 110 from a cloud drive or may be selected from a website or any third party application. Once the media file XYZ.MPEG is uploaded or selected by the user 102, the server system 110 may or may not start playing the media file XYZ.MPEG based on a request received from the user device 104. The server system 110 may then provide a plurality of pattern creation options on a user interface (UI) of user device 104 for facilitating creation of at least one pattern for the media file XYZ.MPEG while playing the media file XYZ.MPEG. In an embodiment, the plurality of pattern creation options includes, but are not limited to, a drag and drop option, a touch panel option, a virtual keys option, and/or a keyboard keys option. The user 102 may then create a pattern for the media file XYZ.MPEG as per the desire or preference of the user 102 using any one of a pattern creation option of the plurality of pattern creation options. In one embodiment, the user 102 can also provide a name for the created pattern and the created pattern is saved under the provided name.

Once the adult entertainment device 106 is connected with the user device 104, the user 102 may select the same media file XYZ.MPEG on the UI of the user device 104. Upon selection of the media file XYZ.MPEG, the server system 110 may display the plurality of script files associated with the selected media file XYZ.MPEG on the UI. The server system 110 may then facilitate the selection of a script file from the plurality of script files by the user 102. This may result in sending of a media play request to the server system 110. The server system 110 may play the media file XYZ.MPEG associated with the selected script file and may send at least one intensity instruction signal set including one or more intensity instruction signals created corresponding to the selected script file to the adult entertainment device 106 connected to the user device 104.

Thereafter, the adult entertainment device 106 customizes successive predefined acts based on the intensity instruction signals to perform at least one predefined act as a successive series with different amplitudes in synchronization with the media file being played, thereby providing a sexual experience as per the needs of the user 102. The predefined act can include one or more combinations of vibration, rotation, swinging, inhalation, temperature variation, expansion, suction contraction and the like.

Figure 12:
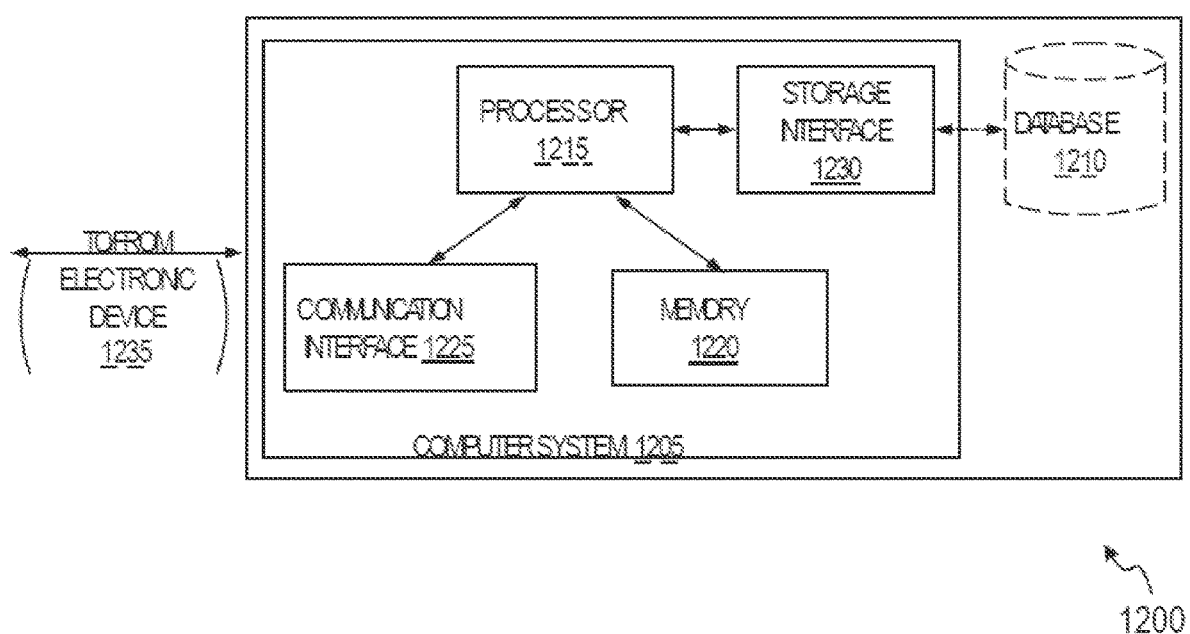
FIG. 12 is a block diagram of a server system, in accordance with an example embodiment of the present disclosure.

It is noted that the instructions (or the executable code) configuring the application may be stored in a memory of the server system 110 and the instructions may be executed by a processor (for example, a single-core or a multi-core processor) included within the server system 110, as is exemplarily shown with reference to FIG. 12. Accordingly, even though the various functionalities for facilitating pattern creation for a multimedia file are explained with reference to or being performed by the server system 110 coupled to the user device 104, it is understood that the processor in conjunction with the code in the memory is configured to execute the various tasks as enabled by the instructions is facilitated by the server system 110.

Figure 2:
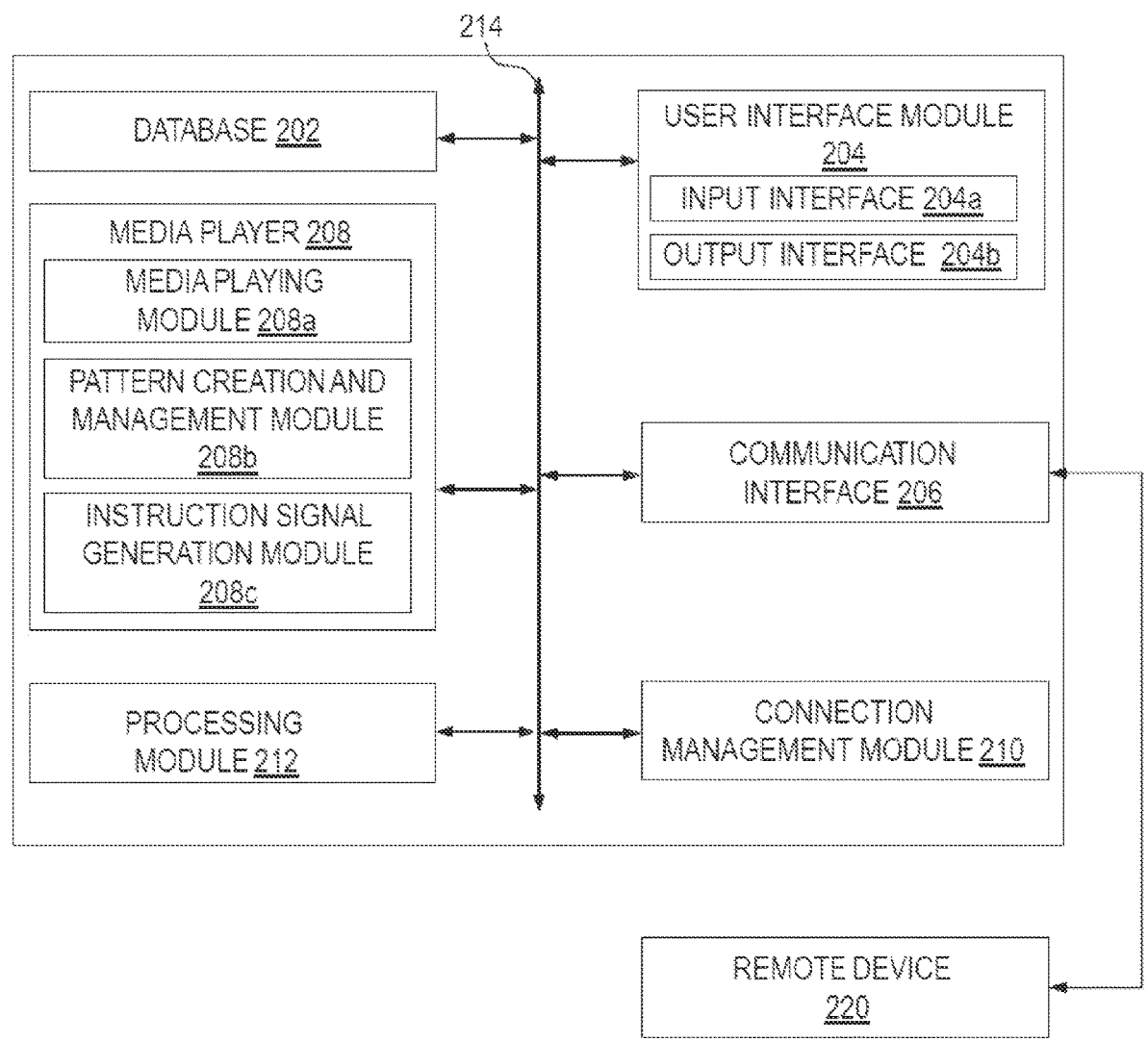
FIG. 2 is a block diagram of an application system for creating patterns for an adult entertainment device, in accordance with an example embodiment of the present disclosure.

FIG. 2 is a block diagram of a system 200 for creating patterns for an adult entertainment device (e.g., the adult entertainment device 106), in accordance with an example embodiment. The system 200 may be a server, such as the server system 110 configured to facilitate the creation of one or more patterns for the media file. The created patterns may further be used to perform at least one predefined act of the adult entertainment device at different amplitudes connected with a user device (e.g., the user device 104). In an embodiment, the system 200 includes a database 202, a user interface (UI) module 204, a communication interface 206, a media player 208, a connection management module 210, a processing module 212 and a centralized circuit system 214.

The database 202 may be configured to store a plurality of patterns of at least one predefined act created for each media file of a plurality of media files by one or more users (e.g., the users 102a and 102b). The database 202 may also be configured to store a plurality of script files created corresponding to the plurality of patterns of each media file of the plurality of media files. In one embodiment, the database 202 stores the plurality of script files as a list of local script files. Further, the database 202 may be configured to store user details associated with each user of the plurality of users. The user details may include, but are not limited to, email-id of the user and the name of the user.

The UI module 204 is in communication with the database 202. The UI module 204 is configured to present one or more UIs for performing various features of the present disclosure including facilitating the creation of one or more patterns for the media file. The UI module 204 may include an input interface 204a and an output interface 204b. The input interface 204a may be configured to receive media files that the users wish to upload. The input interface 204a may also be configured to receive patterns created for each media file. The input interface 204a may also be configured to receive user details associated with each user. Further, the input interface 204a may also be configured to receive media play requests for playing the media files, media selection requests for selecting the media files, and connection requests for connecting the adult entertainment device with the user devices associated with one or more users (e.g., the users 102a and 102b) of the system 200.

Additionally, the input interface 204a may be configured to receive user details associated with users of the system 200. Examples of the input interface 204a may include but are not limited to, a keyboard, a mouse, a joystick, a keypad, a touch screen, soft keys, a floppy disk, a pen drive, a hard drive and the like. In an embodiment, the output interface 204b is configured to display a list of script files associated with a selected media file associated with one or more predefined acts. The output interface 204b may also be configured to display a plurality of pattern creation options for facilitating pattern creation. Further, the output interface 204b is configured to display a list of adult entertainment devices that are available for connection with a user device. Examples of the output interface 204b may include, but are not limited to, a display such as a light emitting diode (LED) display, a thin-film transistor (TFT) display, a liquid crystal display, an active-matrix organic light-emitting diode (AMOLED) display, and the like.

The communication interface 206 is configured to enable communication with a remote device 220, such as the user device 104 and/or the adult entertainment device 106 by exchanging requests, responses, instruction signals, and other messages.

The media player 208 may be in communication with the database 202, the UI module 204 and the communication interface 206. The media player 208 may be configured to play multimedia files, wherein the multimedia content can be recorded files retrieved from the local storage, remote storage or a live broadcast. The media player 208 may also be configured to facilitate the creation of patterns for the played multimedia file. The media player 208 may include a media playing module 208a, a pattern creation and management module 208b, and an instruction signal generation module 208c (hereinafter referred to as modules 208a to 208c).

The media playing module 208a may be configured to play the media file based on a media play request received from the remote device 220. The media playing module 208a may be configured to play a selected media file associated with a selected script file. In an embodiment, the selected media file may be played by the media playing module 208a for facilitating the creation of a pattern for the media file being played. In another embodiment, the selected media file is played by the media playing module 208a for facilitating viewing of the selected media file in the remote device 220 that further sends one or more intensity instruction signals to the adult entertainment device connected with the remote device 220.

The pattern creation and management module 208b is configured to create the pattern for the media file being played based on pattern inputs provided by the user using a pattern creation option of the plurality of pattern creation options. The pattern creation and management module 208b may also be configured to store the created pattern in a script file created for the pattern. The script file may be further stored in the database 202.

The instruction signal generation module 208c may be in communication with the pattern creation and management module 208b. The instruction signal generation module 208c may be configured to create an intensity instruction signal set by transforming the control pattern to sequentially perform at least one predefined act or a series of plurality of predefined acts at different amplitudes present in the selected script file to the one or more intensity instruction signals by the pattern creation and management module 208b. The intensity instruction signal sets may be generated when the adult entertainment device is connected with the remote device 220 and the user has selected and played a multimedia file. In an example embodiment, the created pattern includes at least one intensity instruction signal set that actuates the sexual stimulation device to sequentially perform a series of different amplitudes of the predefined act. The different ranges of the amplitude intensity instruction signal together make the intensity instruction signal set. The intensity instruction signals may be configured to cause customization of the predefined act, such as vibration, rotation, swinging, inhalation, temperature variation, expansion, suction, and contraction of the adult entertainment device to be in synchronization with the multimedia file being played.

The connection management module 210 may be configured to connect the system 200 with the adult entertainment device. In an embodiment, the connection management module 210 may use Bluetooth, Infrared or radio wave technology for connecting the system 200 with the adult entertainment device. The connection management module 210 may also be configured to manage the connection between the adult entertainment device and the system 200 while the user is using the adult entertainment device. Further, the connection management module 210 may be configured to maintain details about the adult entertainment devices that are being connected to the system 200.

The processing module 212 may be in communication with the database 202, the UI module 204, the communication interface 206, the connection management module 210 and the modules 208a to 208c of the media player 208. The processing module 212 may be configured to send operating instructions to the database 202, the UI module 204, the communication interface 206, the connection management module 210 and the modules 208a to 208c of the media player 208 for facilitating the creation of patterns for the multimedia file and for operating the adult entertainment device based on the control patterns created for the media file. For example, the created control patterns may sync vibrations/movements generated by the adult entertainment device with movement of a character displayed in the played multimedia file, thereby enhancing the pleasure of the user using the adult entertainment device.

The database 202, the UI module 204, the communication interface 206, the connection management module 210, the modules 208a to 208c of the media player 208 and the processing module 212 may be configured to communicate with each other via or through the centralized circuit system 214. The centralized circuit system 214 may include various devices configured to, among other things, provide or enable communication among the modules (202-212) of the system 200. In certain embodiments, the centralized circuit system 214 may be a central printed circuit board (PCB) such as a motherboard, a main board, a system board, or a logic board. The centralized circuit system 214 may also, or alternatively, include other printed circuit assemblies (PCAs) or communication channel media. In some embodiments, the centralized circuit system 214 may include appropriate storage interfaces to facilitate communication among the modules (202-212). Some examples of the storage interface may include, for example, an Advanced Technology Attachment (ATA) adapter, a Serial ATA (SATA) adapter, a Small Computer System Interface (SCSI) adapter, a RAID controller, a SAN adapter or a network adapter.

Figure 3:
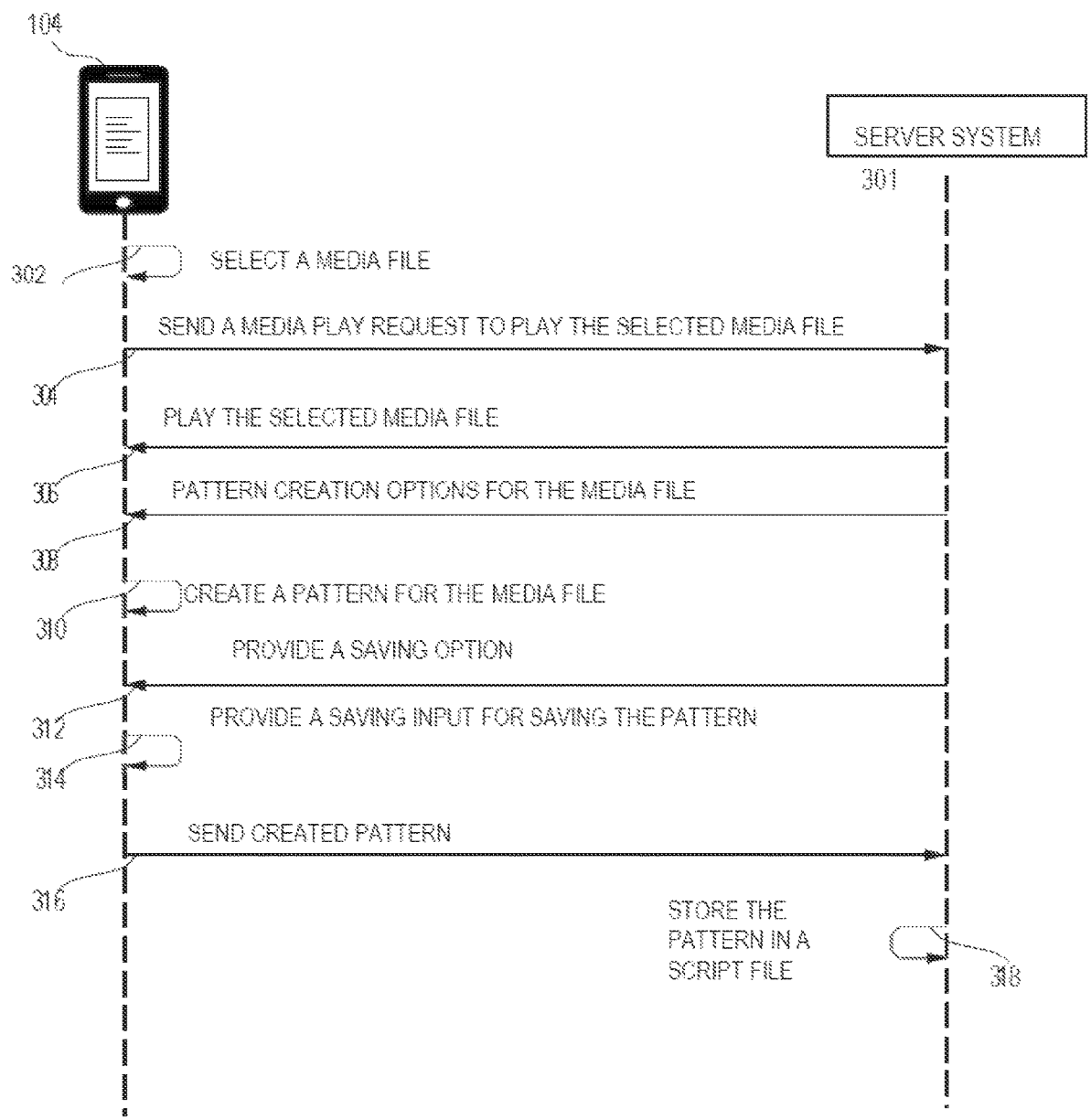
FIG. 3 is a sequence flow diagram for facilitating the creation of a pattern for a multimedia file, in accordance with an example embodiment of the present disclosure.

FIG. 3 is a sequence flow diagram 300 for facilitating the creation of a pattern for a multimedia file, in accordance with an example embodiment. The steps of the sequence flow diagram 300 may be performed when the user 102 wishes to create a pattern for a multimedia file through server system 110 using the user device 104. The steps of the sequence flow diagram 300 may be executed in any suitable order. Further, one or more steps may be grouped together and performed in form of a single step, or one step may have several sub-steps that may be performed in parallel or in a sequential manner. The server system 110 (also an example of the system 200) is referred to as a server system 301 is communicably coupled to the user device 104.

At 302, a user (e.g., the user 102), using a UI provided by the server system 301 on a user device (e.g., the user device 104), may select a multimedia file for which the user 102 wants to create a pattern from a plurality of media files that may be available on a local drive of the user device 104 or access through the network from a remote server (such as web extension or web site).

At 304, a multimedia file access request to access the selected media file is sent to the server system 301 from the user device 104. The media access request includes the selected multimedia file.

At 306, the server system 301, upon receiving the multimedia access request, retrieves and displays the selected media file on the user device 104. At 308, the server system 301 provides a plurality of pattern creation options on the UI provided by the server system 301 for facilitating the creation of a pattern for the selected media file while playing the selected media file.

At 310, the user 102 creates at least one control pattern for a predefined act of the selected multimedia file using at least one pattern creation option that are provided by the server system 301.

At 312, the server system 301 provides a saving option on the UI for saving the created control pattern. At 314, the user 102 provides a saving input for saving the control pattern either as the public pattern or the private pattern. At 316, the control pattern is stored on a server system 301 in a corresponding script file so that the pattern is available for use by the user 102.

Figure 4:
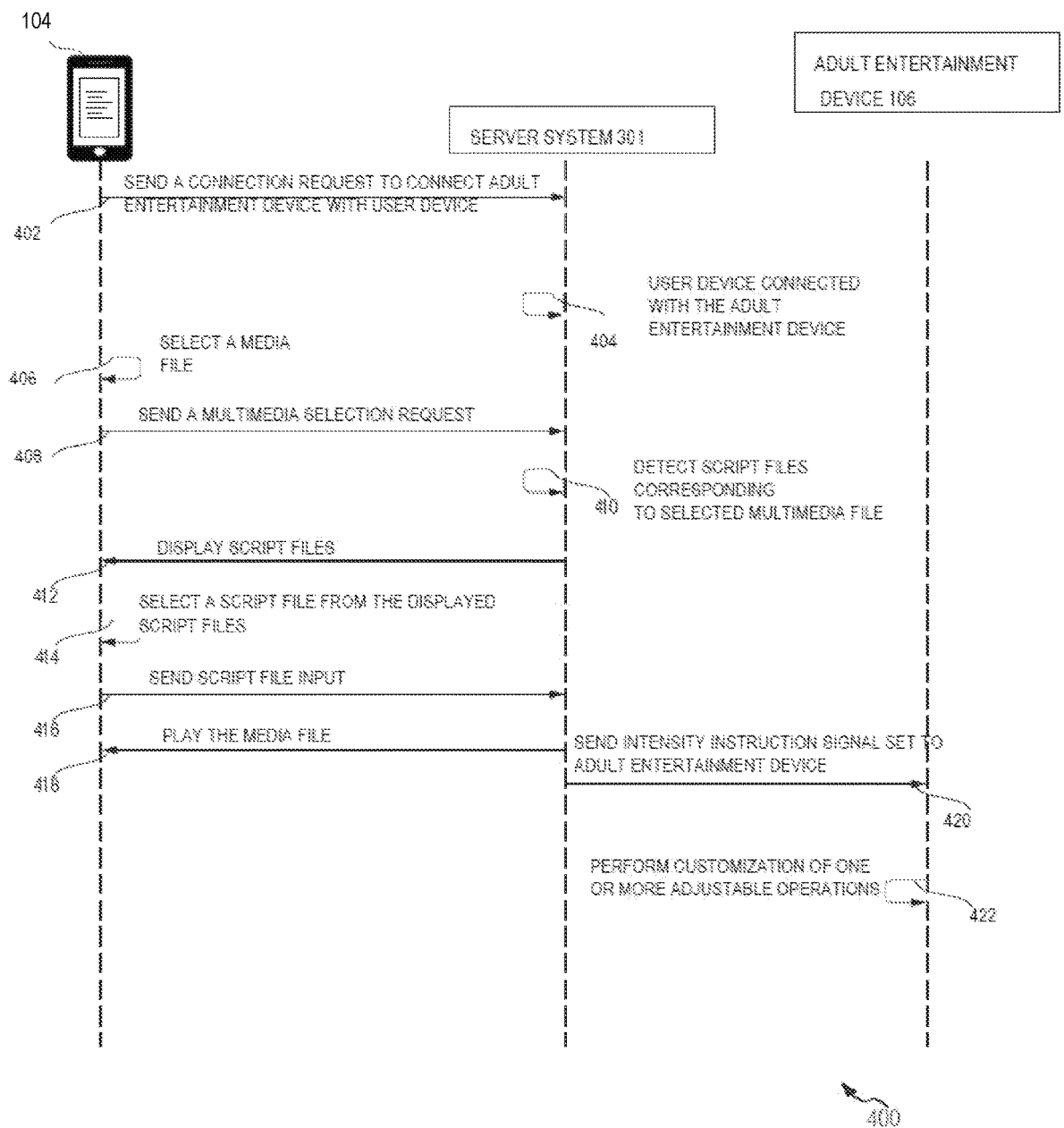
FIG. 4 is a sequence flow diagram for playing the pattern of the multimedia file while using the adult entertainment device, in accordance with an example embodiment of the present disclosure.

FIG. 4 is a sequence flow diagram 400 for playing at least one created control pattern of the multimedia file while using the adult entertainment device (e.g., the adult entertainment device 106) connected with a user device (e.g., the user device 104), in accordance with an example embodiment. The steps of the sequence flow diagram 400 are performed when a user (e.g., the user 102) wants to experience a real-time feeling of engagement while using the adult entertainment device 106. The steps of the sequence flow diagram 400 may be executed in any suitable order. Further, one or more steps may be grouped together and performed in form of a single step, or one step may have several sub-steps that may be performed in parallel or in a sequential manner.

The server system 110 is referred to as an server system 301 and may be communicably coupled to the user device 104 and the adult entertainment device 106.

At 402, a user, using a UI provided by the server system 301 on the user device 104, sends a connection request to the server system 301 to communicably connect the user device 104 with the adult entertainment device 106 associated with the user 102. The connection request may include a device ID associated with the adult entertainment device 106.

At 404, upon receiving the connection request, the user device 104 connects with the adult entertainment device 106 from available one or more adult entertainment devices based on the device ID of the adult entertainment device 106.

At 406, when the adult entertainment device 106 gets connected with the user device 104, the user 102 selects a multimedia file that the user 102 wants to play using the UI provided by the server system 301 in the user device 104. At 408, the selection of the multimedia file generates a multimedia access request that is sent to the server system 301. The multimedia access request may include the media file selected by the user 102.

At 410, the server system 301 detects script files that are available corresponding to the selected multimedia file on the user device 104 and on the server 110. The detected script files can be a combination of script files that are created by the user 102. At 412, the application system 301 displays the script files on the UI presented on the user device 104.

At 414, the user 102 selects a script file from the displayed script files. The selected script file includes a corresponding control pattern that the user wants to play for the selected media file. At 416, the selection of the script file generates a script file input that is sent to the server system 301. The script file input includes the selected script file.

At 418, upon receiving selection input, the server system 301 starts playing the multimedia file associated with the selected script file on the user device 104. At 420, the server system 301 sends one or more intensity instructions signal set transformed from the control pattern in the selected script file to the adult entertainment device 106 for performing at least one predefined act. At least one varying amplitude pattern of the pattern in the selected script file may be transformed into the intensity instructions signal set (e.g., series of different amplitude intensity instruction signals). The series of varying amplitude intensity instruction signal sets are then sent to the adult entertainment device 106.

In an embodiment, the step 422 is performed simultaneously with the step 420. At 422, the adult entertainment device 106, upon receiving the intensity instructions signals, transforms the control pattern to sequentially perform at least one predefined act or a series of a plurality of predefined acts at different amplitudes present in the selected script file to the one or more intensity instruction signals and performs customization of one or more adjustable operations to be in synchronization with the selected media file associated with the selected script file. The at least one amplitude intensity instruction signal set that is received from the application system 301 may customize at least one of a vibration, rotation, swing, temperature, expansion, suction, inhalation, and contraction of the adult entertainment device 106 based on the amplitude pattern of the selected pattern for the played multimedia file. The synchronization of the predefined act with the played multimedia file may ensure that movements of a character in the played multimedia file are synced with the operation of the adult entertainment device 106, thereby providing a real-time feeling of engagement to the user 102 using the adult entertainment device 106.

Figure 5:
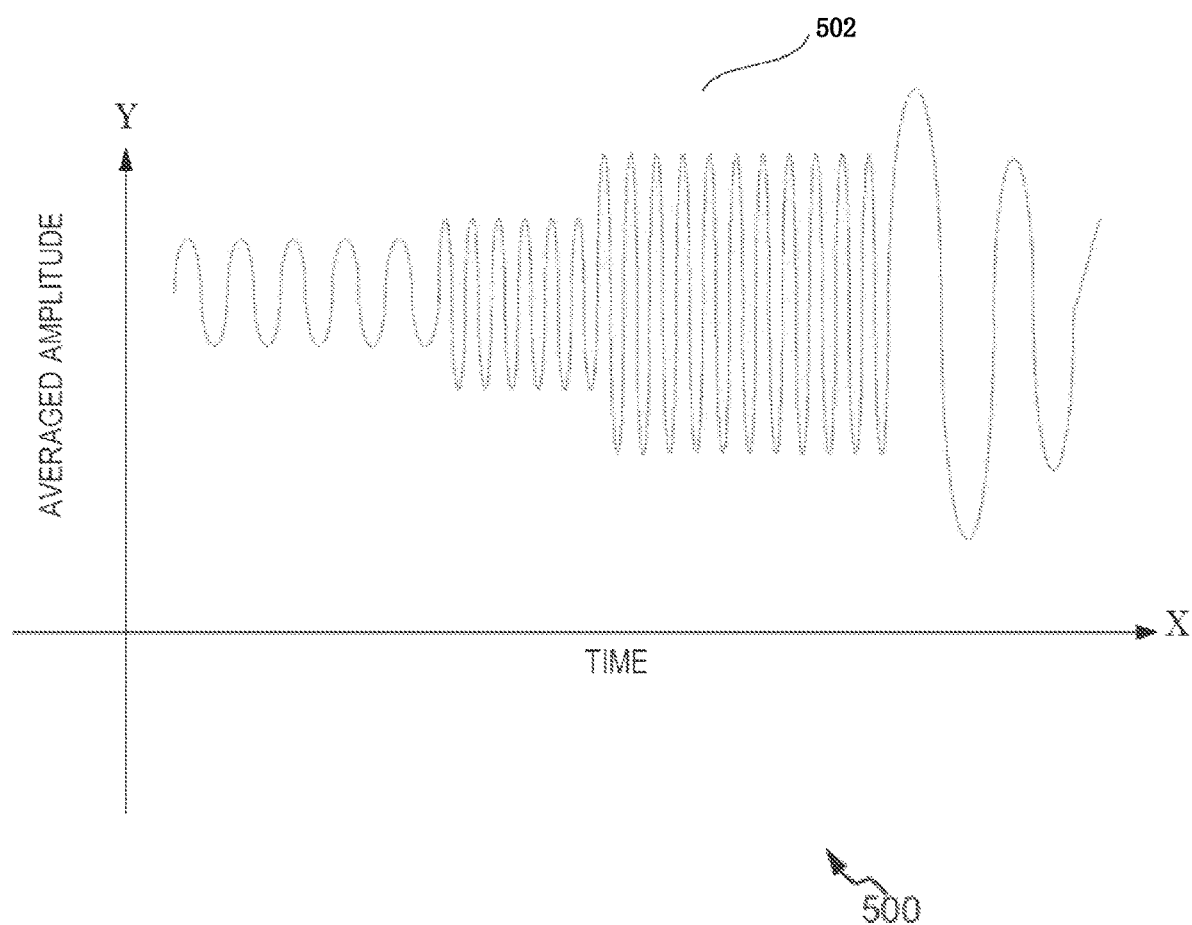
FIG. 5 is a graphical representation of the pattern created for the multimedia file, in accordance with another example embodiment of the present disclosure.

FIG. 5 is a graphical representation 500 of an example of a control pattern created for a multimedia file using the server system 110 (also known as server system 200 and server system 301), in accordance with an example embodiment. The control pattern created for the media file may be a combination of different amplitudes is represented as an average amplitude curve 502 correlated to the multimedia file and at varying periods the amplitude pattern also varies corresponding to the control pattern associated with the content of the multimedia file being played. The average amplitude curve 502 in the pattern may be further used to create the at least one amplitude intensity instruction signal set for causing customization of the varying amplitudes of the adjustable operations for an adult entertainment device (e.g., the adult entertainment device 106) connected with a user device (e.g., the user device 104) while playing the pattern created for the multimedia file on the user device.

Figure 6:
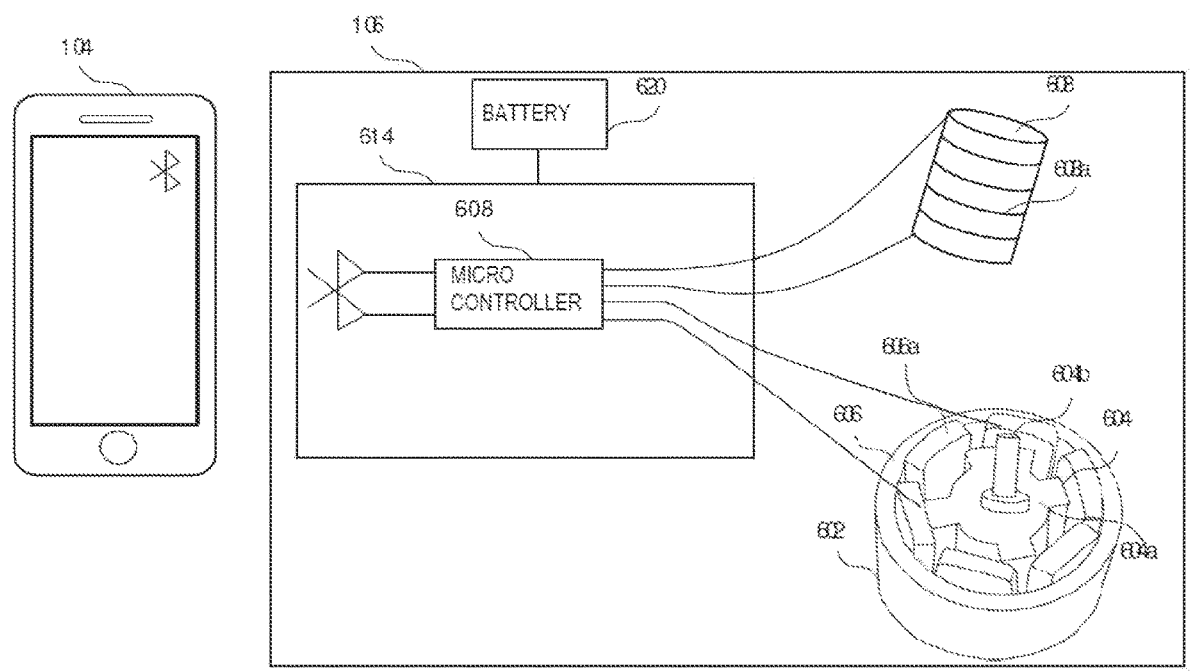
FIG. 6 is a schematic representation depicting various components of the adult entertainment device electronically connected with the user device, in accordance with an example embodiment of the present disclosure.

FIG. 6 is a schematic representation 600 depicting various components of an adult entertainment device (e.g., the adult entertainment device 106) electronically connected with a user device (e.g., the user device 104), in accordance with an example embodiment of the present disclosure. The adult entertainment device 106 can be a male entertainment device or a female entertainment device. The functioning of the adult entertainment device 106 may vary depending on the type of the adult entertainment device.

In an example embodiment, the adult entertainment device 106 includes a motor 602, an electromagnet 608, a printed circuit board (PCB) 614, a battery 620 and a plurality of wires for electrically connecting different components of the adult entertainment device 106.

In an example embodiment, the motor 602 may be an eccentric rotating mass vibration motor (ERM) that uses a small unbalanced mass on a direct current (DC) motor so that when the motor 602 rotates, a force is created that transforms into vibrations (an example of an adjustable parameter of the adult entertainment device 106). The motor 602 may include a rotor 604 and a stator 606. The rotor 604 may further include a permanent magnet 604a and a shaft 604b that are assembled together as shown in the FIG. 6. So for example, if the permanent magnet 604a rotates, the shaft 604b will automatically rotate with the permanent magnet 604a. The stator 606 may include windings 606a. The windings 606a may be electrically connected with the PCB 614 using one or more wires of the plurality of wires. The PCB 614 may provide and control electricity passing through the windings 606a. The windings 606a, upon receiving the electricity from the PCB 614, generate the magnetic field and the generated magnetic field rotates the permanent magnet 604a provided in the rotor 604 that further rotates the shaft 604b assembled with the permanent magnet 604a.

The rotation of the shaft 604b causes rotation of an unbalanced mass attached to the shaft 604b that further generates vibrations by transforming the force created due to the rotation of the unbalanced mass. Therefore, if the electric current that passes through the windings 606a is controlled, the vibration frequency of the adult entertainment device 106 can also be controlled. The vibration amplitude depends on the weight of the unbalanced mass attached to the shaft 604b as the vibration amplitude is directly proportional to the weight of the unbalanced mass.

In order to control the vibration amplitude, the electromagnet 608 is provided in the adult entertainment device 106. In an embodiment, the electromagnet 608 is a magnet that includes a piece of metal that is surrounded by a coil 608a. Examples of the metal that can be used for creating the electromagnet 608 include, but are not limited to, iron and steel. The coil 608a of the electromagnet 608 may be electrically connected with the PCB 614 using the one or more wires of the plurality of wires. The PCB 614 provides and controls electricity passing through the coil 608a. The coil 608a, upon receiving the electricity from the PCB 614, generates the magnetic field as the magnet of the electromagnet 608 becomes magnetic. The magnetic field generated by the magnet causes magnetic attraction to the unbalanced mass, which further changes the vibration amplitude. If the electric current that passes through the coil 608a is controlled, the magnetic field intensity of the electromagnet 608 can be controlled that further controls the vibration amplitude.

As explained in the previous figures, the pattern may include a series of amplitude patterns that are transformed into corresponding intensity instruction signal set. The intensity instruction signal set may be further communicated to a microcontroller 612 provided in the PCB 614 of the adult entertainment device 106 using a communication technology. The intensity instruction signals include at least one at least one amplitude intensity instruction signal set with at least one or more different amplitude series. Examples of the communication technology include, but are not limited to, Bluetooth technology, Infrared technology and radio wave technology.

The microcontroller 612 determines the same or different controls for each of the intensity instruction signal set based on the control pattern received from the server system 110. For example, to achieve a certain wave pattern/shape for a control pattern, the microcontroller 612 may operate the motor 602 initially at a first amplitude and after a certain duration of the played multimedia file the motor 602 operates at a second different amplitude and/or frequency, thereby forming a series of different amplitudes of at least one predefined act or a successive series of predefined acts. The microcontroller 612 may control the electricity provided to the windings 606a based on the at least one amplitude intensity instruction signal received from the user device 104 thereby controlling at least one amplitude-based predefined act of the unbalanced mass provided in the adult entertainment device 106 as the electric current passing through the windings 606a controls the functioning of the motor 602. The amplitude-based predefined acts operating at varying amplitudes may include vibration, rotation, swing, temperature, expansion, suction, inhalation, and contraction of the adult entertainment device 106.

Further, the microcontroller 612 may control the electricity provided to the coil 608a based on the at least one amplitude intensity instruction signal received from the user device 104 thereby controlling at least one amplitude-based predefined act of the unbalanced mass provided in the adult entertainment device 106 as the electric current passing through the coil 608a controls the intensity of magnetic field generated by the electromagnet 608.

The battery 620 may be configured to provide electrical power to the PCB 614 that further uses the electrical power for operation of the adult entertainment device 106.

Figure 7A:
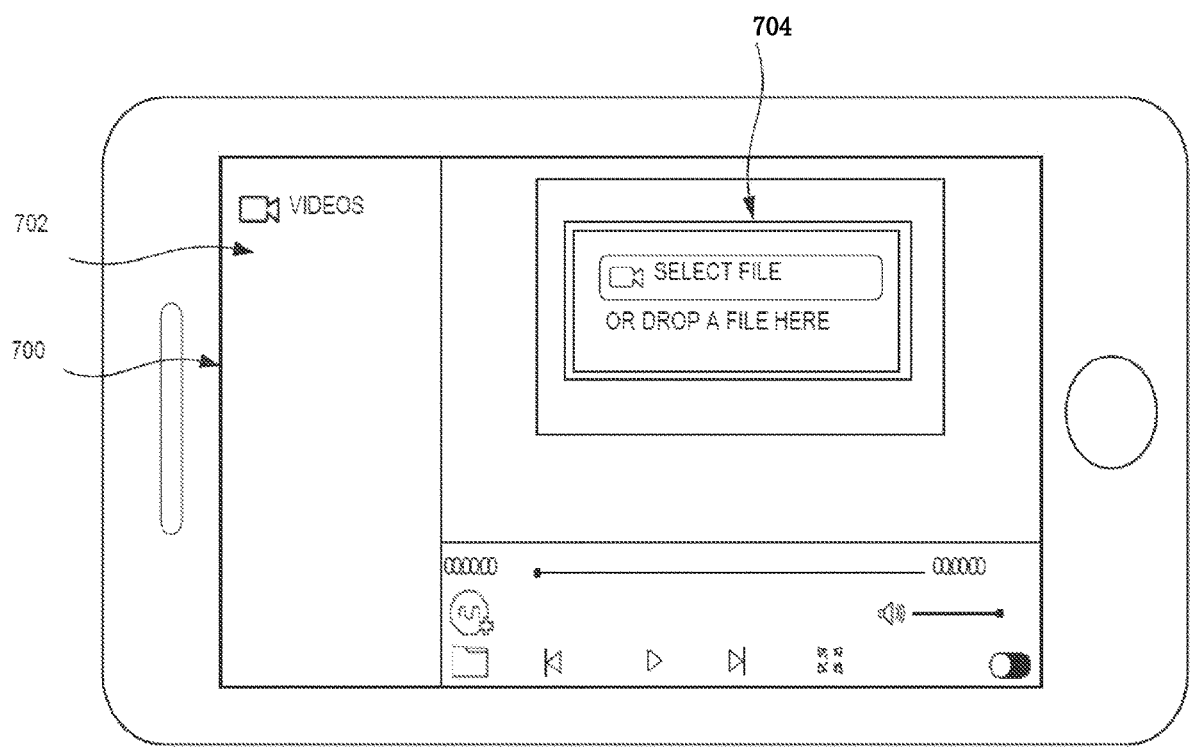
FIGS. 7A to 7C, collectively, represent an example representation of a process to be followed for creating a control pattern for a multimedia file with corresponding User Interfaces (UIs), in accordance with an example embodiment of the present disclosure.
Figure 7B:
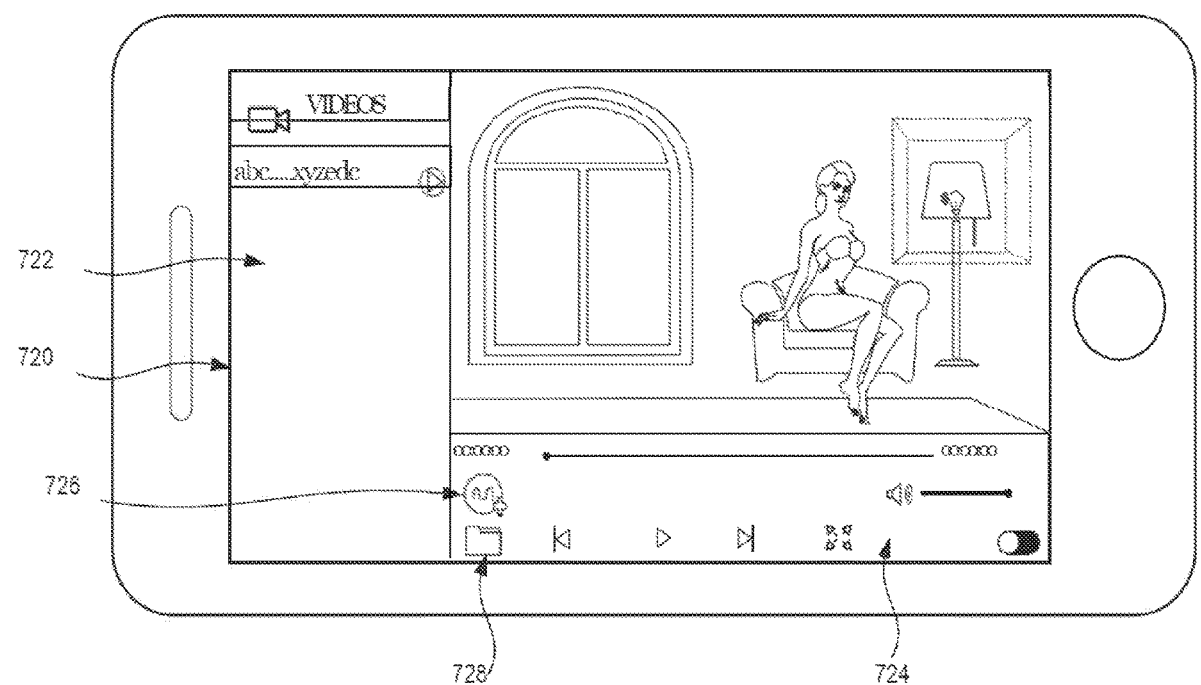
Figure 7C:
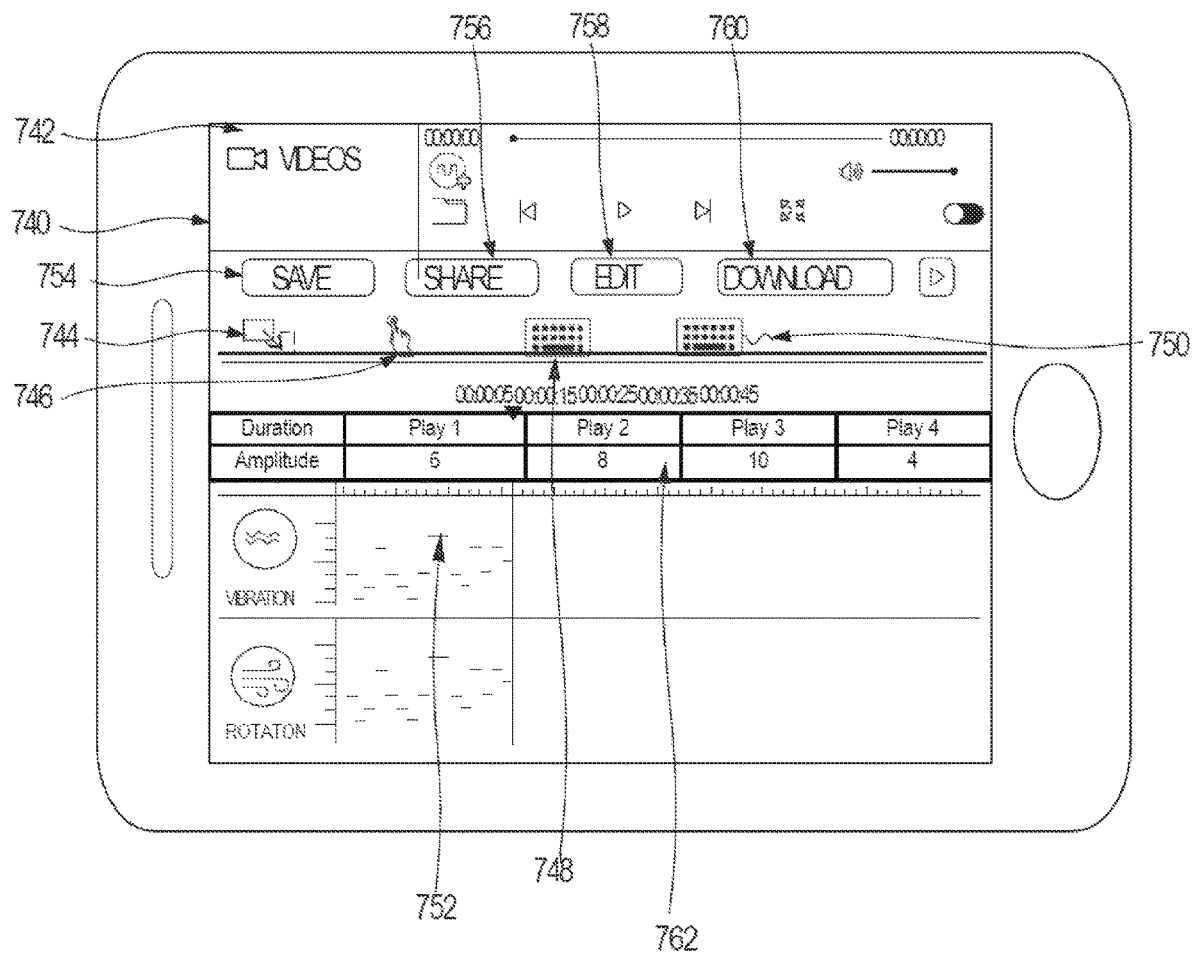

FIGS. 7A to 7C, collectively, represent an example representation of a process to be followed for creating a pattern for a media file with corresponding User Interfaces (UIs), in accordance with an example embodiment of the present disclosure.

A UI 700 may display a multimedia selection/upload page 702 as facilitated by the server system 110. The user 102 can select/upload a multimedia file for which the user 102 wants to create a control pattern using the multimedia select/upload page 702 displayed on the user device 104. The page 702 may display a select file tab 704. The user 102 can click on the select file tab 704 for accessing a multimedia file from a local drive of the user device 104 or remote storage. Clicking on the select file tab 704 opens a screen with one or more links or tabs to select the specific multimedia file the user wants to access. The user selects a selects or can drag and drop the multimedia file that is to be uploaded for creating or editing one or more control patterns.

As shown in FIG. 7B, a UI 720 may display a multimedia play page 722 as facilitated by the server system 110. The media play page 722 may include a video player 724 where the multimedia file to be played is shown. The video player 724 may also include a pattern creation icon 726 and an import video icon 728. The user 102 can click on the pattern creation icon 726 for creating the pattern for the media file played on the video player 724 and the user can click on the import video icon 728 for uploading additional videos. Clicking on the pattern creation icon 726 may redirect the user 102 to a pattern creation page 742. The pattern creation page 742 is explained in detail with reference to FIG. 7C.

As shown in FIG. 7C, a UI 740 may display the pattern creation page 742 facilitated by the server system 110. The pattern creation page 742 may include a plurality of pattern creation options in form of icons, such as a drag and drop icon 744, a touch panel icon 746, a virtual keys icon 748 and/or a keyboard keys icon 750 that can be used by the user 102 for creating the pattern. The user 102 can click on the drag and drop icon 744 in case the user 102 wants to drag and drop the created pattern from a different platform. The user 102 can click on the touch panel icon 746 for drawing the pattern directly on a touch panel provided on the pattern creation page 742. The user 102 can click on the virtual keys icon 748 for using a virtual keyboard for creating the pattern. The user can click on the keyboard keys icon 750 for using the hardware keyboard keys for drawing/creating the pattern.

In an example embodiment, the user 102 uses the keyboard keys for creating the pattern for the media file being played in the UI 740. In a non-limiting example, the user 102 may press the keyboard up-key to turn the pattern up and press the keyboard down-key to turn the pattern down for creating the pattern (e.g., a pattern similar to the illustration of FIG. 5) for the media file. It should be noted that the user 102 can set any other keys on a keyboard to replace the keyboard up key and the keyboard down key for creating the pattern while using the keyboard keys option. The user 102 for at least one control pattern can create different controls during different sessions of the multimedia file (such as 762), wherein the user 102 can include (e.g., mention) the amplitude for a predefined act.

In an exemplary scenario, the control pattern created as a series of different amplitudes for a predefined act is shown at 762. The user 102 can partition the multimedia content such as four sessions. During a first control period (i.e., play 1), the adult entertainment device 106 amplitude may be set to '6' for vibration, the second control period (i.e., play 2) the adult entertainment device 106 amplitude may be set to '8', the third control period (i.e., play 3) the adult entertainment device 106 amplitude may be set to '10' and the fourth control period (i.e., play 4) the adult entertainment device 106 amplitude may be set to '4'.

The created pattern may then be displayed in a section 752 of the pattern creation page 742. The pattern creation page 742 may also include a save button 754, a share button 756, an edit button 758 and/or a download button 760. The save button 754 can be clicked by the user for saving the created pattern. Clicking on the save button 754 may open a pop-up box where the user 102 can provide the name for the control pattern and can provide a saving input by making a selection to save the control pattern. Once the user provides information in the pop-up box, the information along with the control pattern is saved in a script file that is further stored either in the user device 104 or in a database associated with the server 110 depending on a saving input provided by the user in the pop-up box.

The share button 756 can be clicked by the user 102 for sharing the created pattern with another person. Clicking on the share button 756 may open a pop-up box where the user 102 can provide an email-id of the person with whom the user 102 wants to share the pattern for sharing the created pattern. Clicking on the edit button 758 may provide the user 102 with one or more editing options such as but not limited to copy, paste, cut and the like for editing the created pattern. Similarly, the download button 760 can be clicked by the user 102 for downloading the pattern on the user device 104.

Figure 8A:
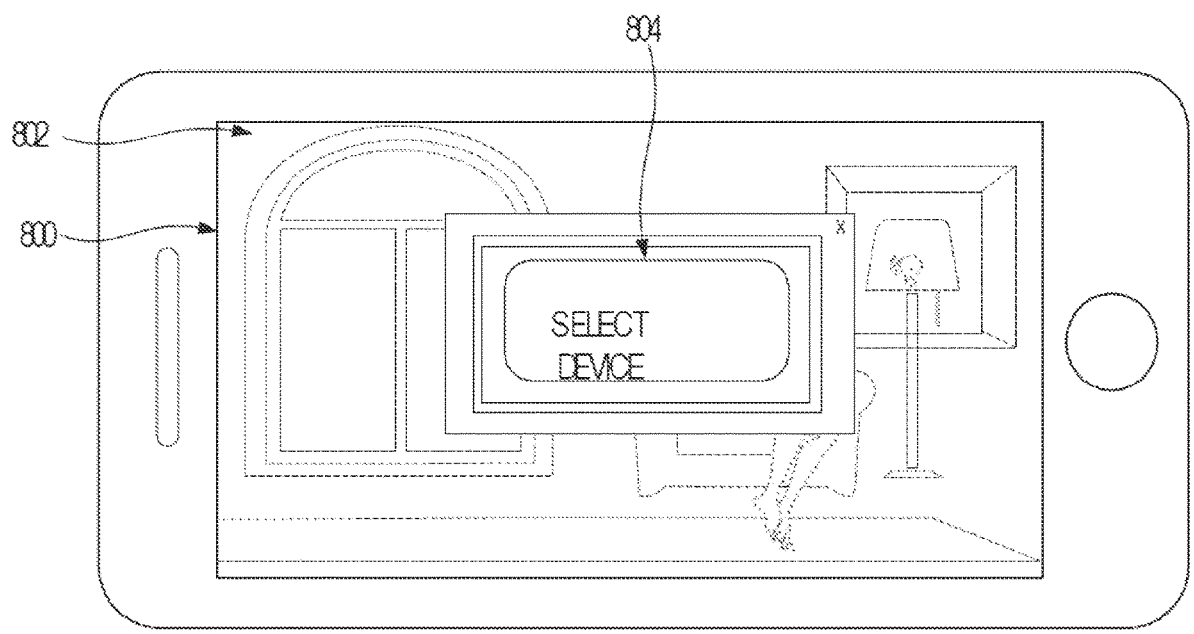
FIGS. 8A to 8C, collectively, represent an example representation of a process to be followed for playing a pattern from a plurality of patterns that are available for the multimedia file while using the adult entertainment device connected with the user device with corresponding UIs, in accordance with an example embodiment of the present disclosure.
Figure 8B:
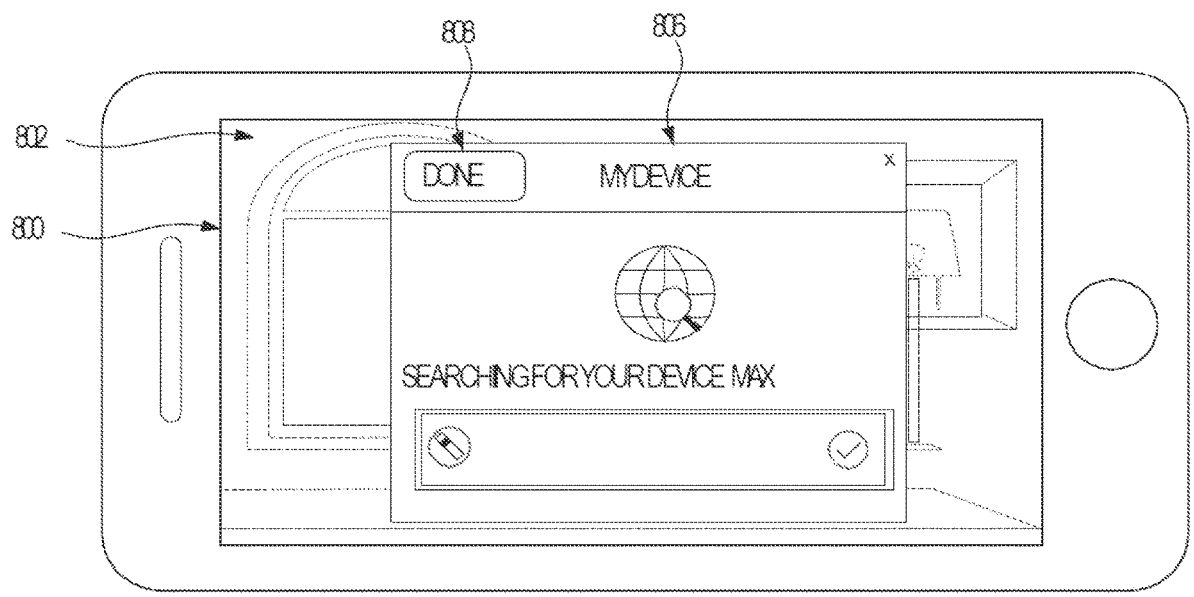
Figure 8C:
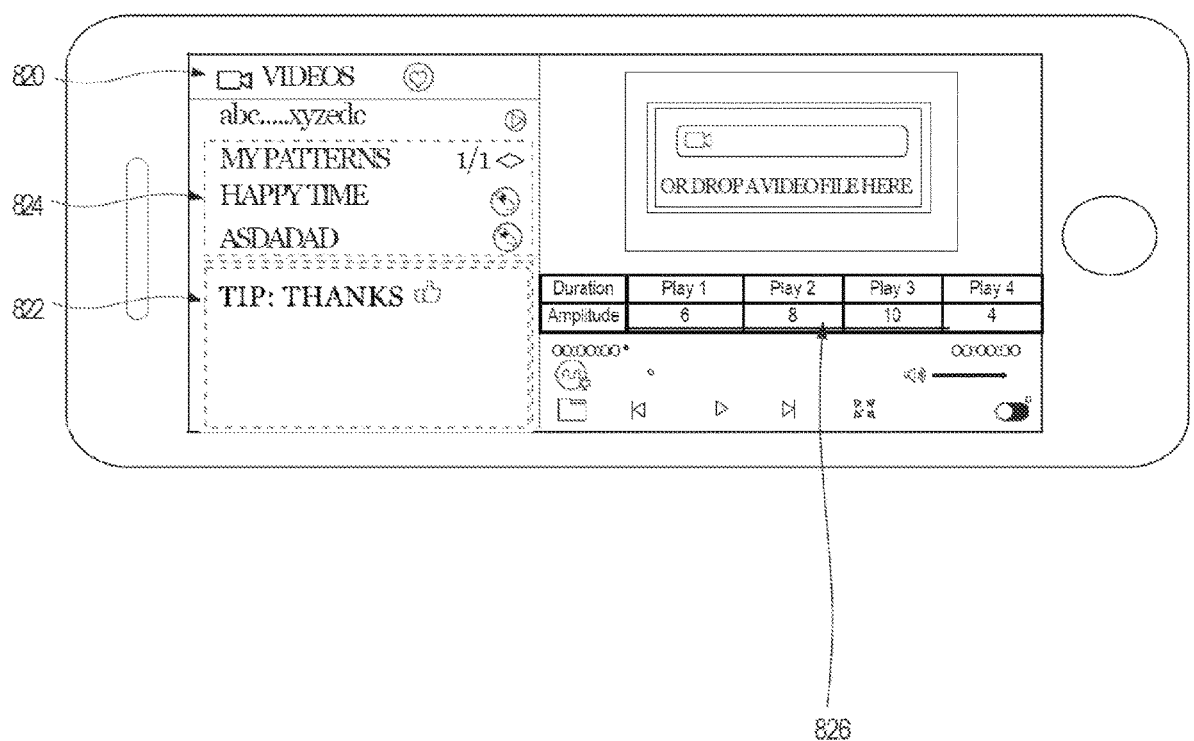

FIGS. 8A to 8C, collectively, represent an example representation of a process to be followed for playing a control pattern from a plurality of patterns that are available for a multimedia file while using an adult entertainment device (e.g., the adult entertainment device 106) connected with a user device (e.g., the user device 104) with corresponding User Interfaces (UIs), in accordance with an example embodiment of the present disclosure.

The UI 800 may display a connection page 802 on the user device 104. The user 102 can connect the adult entertainment device 106 with the user device 104 using the connection page 802 of the media application 112. The connection page 802 may display a select device tab 804. The user 102 can click on the select device tab 804 for connecting the adult entertainment device 106 with the user device 104. Clicking on the select device tab 804 may open a pop-up box 806 (shown in FIG. 8B). The pop-up box 806 may display the name of the devices that are available for connection with the user device.

The user 102 can select a device from the available devices based on the device name and can click on a done button 808 provided in the pop-up box 806 to electronically connect the adult entertainment device 106 with the user device 104. Once the adult entertainment device 106 is connected with the user device 104, the user 102 can select a media file that the user 102 wishes to play as shown in 7A.

Once the user 102 selects the multimedia file to play, the control patterns available for the selected multimedia file may be displayed on a pattern display page 820 shown in FIG. 8C. According to an embodiment, during reproduction of playing the multimedia file with the selected control patterns, the server system 110 may generate a tipping request as a link 822 and display on the page 820, wherein the tipping request may include tipping parameters for a control pattern associated with a predefined act, can vary from a one control pattern to another control pattern and the tipping parameters include specific tip amounts or one or more ranges of tip amounts and predefined acts corresponding thereto. The tip amounts may be virtual rewards, tokens and the like. For example, tip amounts between 1 to 10 tokens may cause the model toy to vibrate at a low speed for play 1, and tip amounts between 11 to 20 tokens may cause the model toy to vibrate at a high speed for play 3.

The user 102 can select a pattern (e.g., any pattern) from the list of control patterns by double-clicking/touching on the pattern. During the duration of playing the multimedia file, the server system 110 after the control pattern is selected may provide instructions or signals to cause the adult entertainment device 106 to start receiving intensity instruction signals corresponding to the selected pattern. The adult entertainment device may then perform customization of successive predefined act as a series at different amplitudes in synchronization with the played media file associated with the selected pattern as explained with reference to FIG. 6.

For example as shown at 822, while playing the multimedia file during a first control period (i.e., play 1), the adult entertainment device 106 may provide an amplitude of '6' for vibration, during the second control period (i.e., play 2) the adult entertainment device 106 may provide an amplitude of '8', during the third control period (i.e., play 3) the adult entertainment device 106 may provide an amplitude of '10' and during the fourth control period (i.e., play 4) the adult entertainment device 106 may provide an amplitude of '4'.

Figure 9:
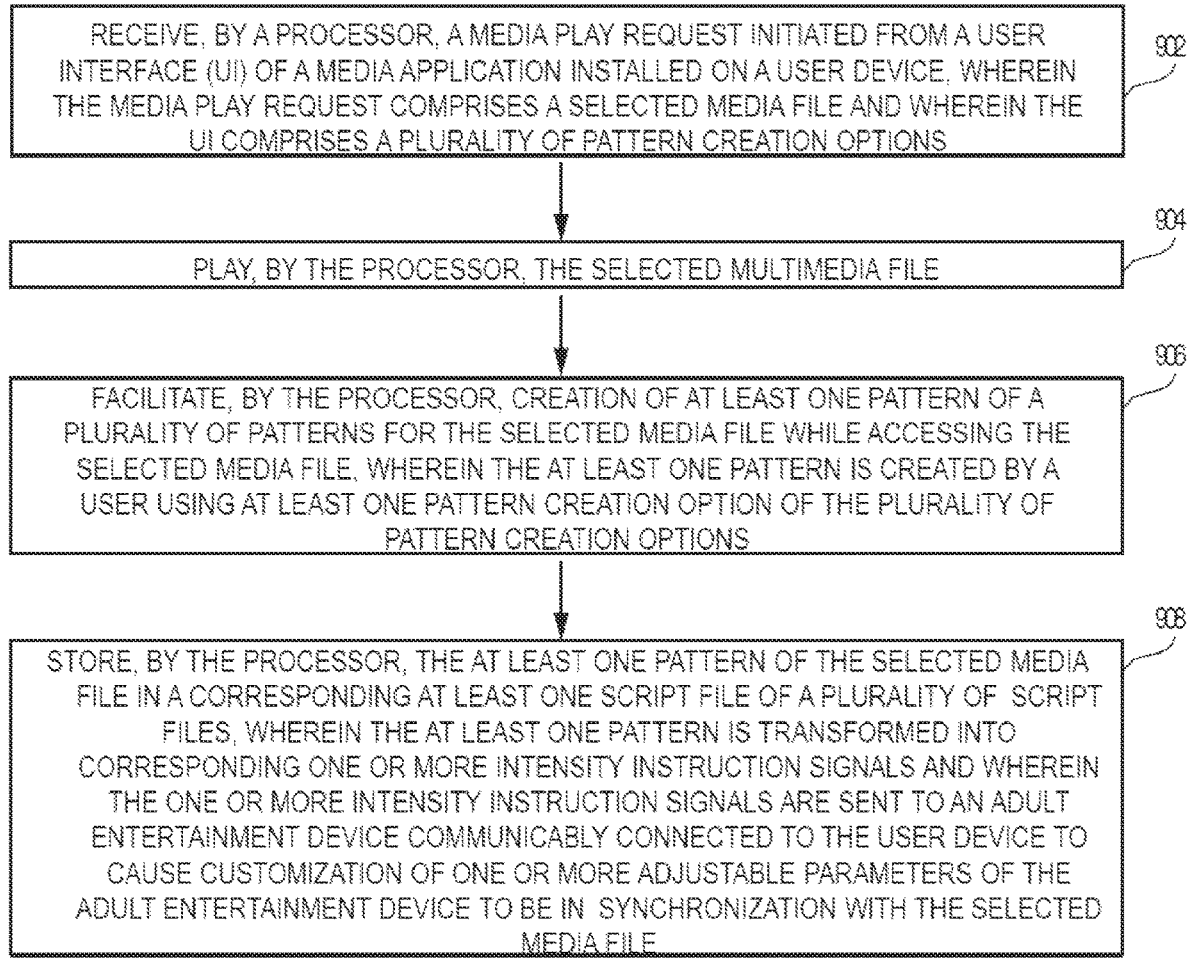
FIG. 9 is a flowchart illustrating a method for creating patterns for the adult entertainment device, in accordance with an example embodiment of the present disclosure.

FIG. 9 is a flowchart illustrating a method 900 for creating at least one pattern for an adult entertainment device (e.g., the adult entertainment device 106), in accordance with an example embodiment. The operations of the method 900 may be carried out by a server such as the server system 110 (also known as the system 200 and/or system 301) or the electronic device 104. The sequence of operations of the method 900 may not be necessarily executed in the same order as they are presented. Further, one or more operations may be grouped together and performed in form of a single step, or one operation may have several sub-steps that may be performed in parallel or in a sequential manner.

At operation 902, the method 900 may include receiving, by a processor, a media play request initiated from a UI of a user device (e.g., the user device 104). A user (e.g., the user 102) may select a media file as a recorded file from a local drive of the user device 104 or remote storage from external webservers for which the user 102 wishes to create a pattern. The media play request may include the selected media file. The UI includes a plurality of pattern creation options that can be used by the user 102 for creating the pattern for the media file.

At operation 904, the method 900 may include accessing, by the processor, the selected media file. The media file included in the media play request may be accessed on the user device 104.

At operation 906, the method 900 may include facilitating, by the processor, a creation of at least one pattern of a plurality of patterns for the selected media file while playing the selected media file. The user may create the at least one pattern of the plurality of patterns using the at least one pattern creation option of the plurality of pattern creation options provided on the UI of the server system 110. The plurality of pattern creation options may include a drag and drop option, a touch panel option, a virtual keys option and a keyboard keys option. While using the drag and drop option, the user 102 can create the pattern using any platform, and the created pattern is dragged and placed in the UI of the server system 110. While using the touch panel option, the user 102 can draw a pattern directly on a touch panel provided in the UI with their fingers and the drawn pattern may be saved as the pattern for the media file. While using the virtual keys option, the user 102 may use keys of a virtual keyboard provided on the UI for creating the pattern. Similarly, in case of the keyboard keys option, the user 102 may use the keyboard keys to create the pattern.

At operation 908, the method 900 may include storing, by the processor, the at least one pattern of the selected media file in a corresponding at least one script file of a plurality of script files. The at least one pattern created by the user 102 may be stored in the at least one script file created for the at least one created pattern. The at least one pattern stored in the at least one script file may be transformed into corresponding one or more intensity instruction signal sets while playing of the media file associated with the at least one script file. The one or more intensity instruction signal sets may then be sent to an adult entertainment device 106 communicably connected to the user device 104 to cause customization of one or more predefined acts as a series at different amplitudes for the adult entertainment device 106 to be in synchronization with the media file being played. The synchronization of the predefined act with the played media file associated with the at least one script file may ensure that movements of a character in the played media file are synced with the operation of the adult entertainment device 106.

FIG. 10 is a flowchart illustrating a method 1000 for playing at least one control pattern of a media file while using an adult entertainment device (e.g., the adult entertainment device 106) for performing a predefined act, in accordance with an example embodiment. The operations of the method 1000 may be carried out by a server such as the server 110 (also known as the system 200 and/or system 301) or the electronic device 104. The sequence of operations of the method 1000 may be executed in any suitable order. Further, one or more operations may be grouped together and performed in form of a single step, or one operation may have several sub-steps that may be performed in parallel or a sequential manner.

At operation 1002, the method 1000 may include receiving, by a processor, a media selection request initiated from a UI of a user device (e.g., the user device 104) communicably connected to the adult entertainment device 106. The media selection request may include a selected media file. A user (e.g., the user 102) may select a media file that the user 102 wishes to play from a plurality of multimedia files that are available may be recorded or a live broadcast facilitated by a server system (e.g., the server system 110).

At operation 1004, the method 1000 may include detecting, by the processor, at least one script file of a plurality of script files corresponding to the selected media file on the user device 104 and on the server system 110. The script files associated with the selected media file may be detected from the local memory of the user device 104 and/or from a database associated with the server system 110.

At operation 1006, the method 1000 may include displaying, by the processor, a list of script files detected from the user device and from the server system. The script files that are detected from the local drive of the user device may be displayed as the list of local script files and the script files that are detected from the database associated with the server system may be displayed as the list of public script files.

At operation 1008, the method 1000 may include receiving, by the processor, a user selection of a script file detected. The user 102 may select the script file that the user 102 wishes to play from the displayed list of script files. The selected script file may include at least one corresponding control pattern associated to at least one predefined act to perform sequentially a series of different amplitudes for the selected media file.

At operation 1010, the method 1000 may include playing, by the processor, the selected media file associated with the selected script file. The media file may be played based on the selected script file.

At operation 1012, the method 1000 may include sending, by the processor, one or more intensity instruction signal sets transformed from the pattern in the selected script file to the adult entertainment device 106. The intensity instruction signal sets that are created based on the control pattern included in the selected script file may be sent to the adult entertainment device 106. Customization of one or more predefined acts at different amplitudes of the adult entertainment device 106 may be provided to be in synchronization with the media file being played. Therefore, the user 102 using the adult entertainment device 106 may experience a real time feeling of engagement as the movements of a character in the played multimedia are synced with the operation of the adult entertainment device 106.

Figure 11:
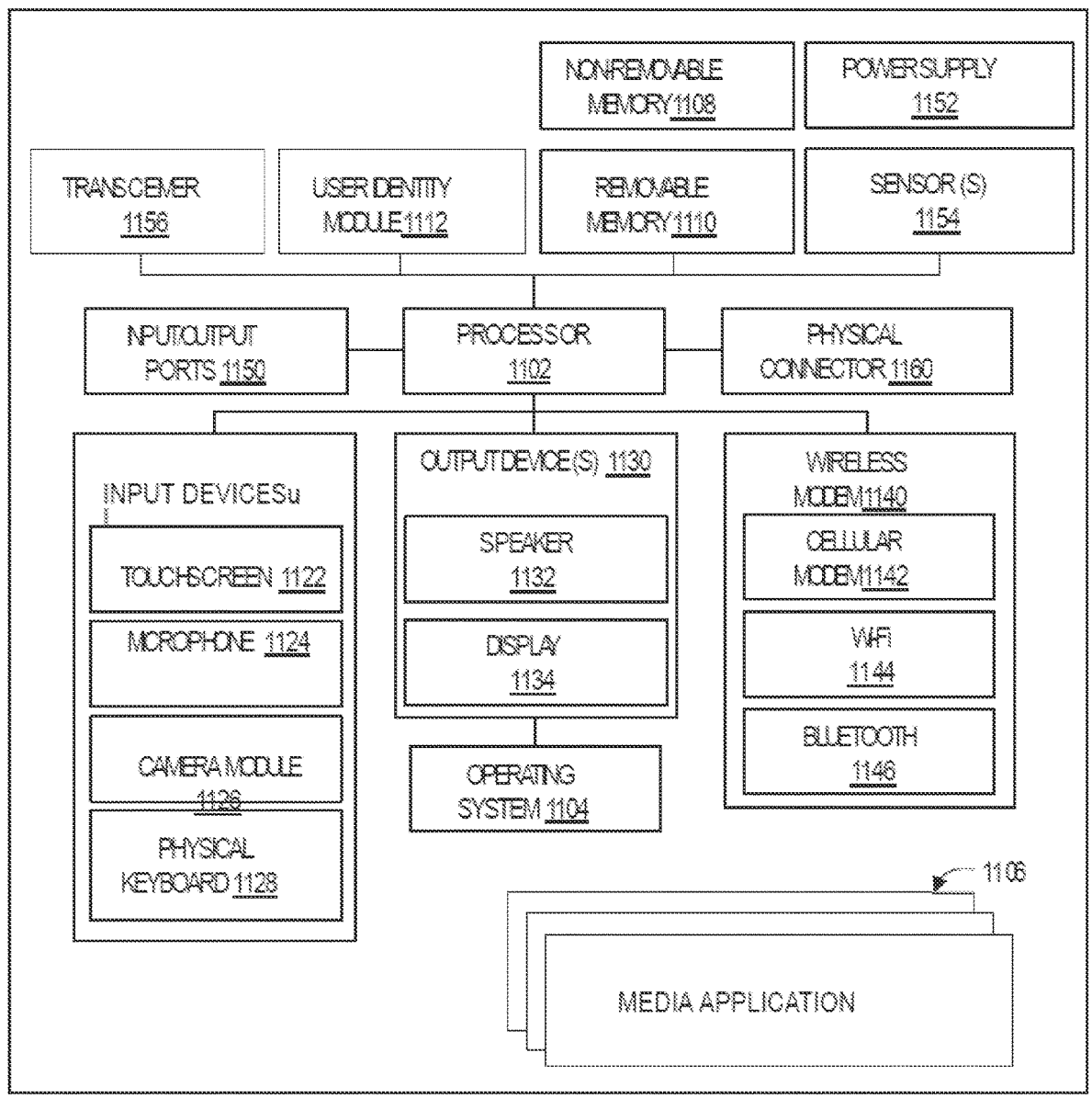
FIG. 11 is a block diagram of an electronic device capable of implementing the various embodiments of the present disclosure, in accordance with an example embodiment.

FIG. 11 shows a simplified block diagram of an electronic device 900 capable of implementing the various embodiments of the present disclosure. The electronic device 1100 may be an example of the electronic devices 104a to 104c or the system 200. It should be understood that the electronic device 1100 as illustrated and hereinafter described is merely illustrative of one type of device and should not be taken to limit the scope of the embodiments. As such, it should be appreciated that at least some of the components described below in connection with the electronic device 1100 may be optional and thus in an example embodiment may include more, less or different components than those described in connection with the example embodiment of the FIG. 11. As such, among other examples, the electronic device 1100 could be any of an electronic device or may be embodied in any of the electronic devices, for example, cellular phones, tablet computers, laptops, mobile computers, personal digital assistants (PDAs), mobile televisions, mobile digital assistants, or any combination of the aforementioned, and other types of communication or multimedia devices.

The illustrated electronic device 1100 may include a controller or a processor 1102 (e.g., a signal processor, microprocessor, ASIC, or other control and processing logic circuitry) for performing such tasks as signal coding, data processing, image processing, input/output processing, power control, and/or other functions. An operating system 1104 may control the allocation and usage of the components of the electronic device 1100 and may provide support for one or more programs such as a media application that implements one or more of the innovative features described herein. The applications 1106 may include common mobile computing applications (e.g., telephony applications, email applications, calendars, contact managers, web browsers, messaging applications such as USSD messaging or SMS messaging or SIM Tool Kit (STK) application) or any other computing application.

The illustrated electronic device 1100 may include one or more memory components, for example, a non-removable memory 1108 and/or a removable memory 1110. The non-removable memory 1108 and/or the removable memory 1110 may be collectively known as storage device/module in an embodiment. The non-removable memory 1108 may include RAM, ROM, flash memory, a hard disk, or other well-known memory storage technologies. The removable memory 1110 can include flash memory, smart cards, or a Subscriber Identity Module (SIM). The one or more memory components can be used for storing data and/or code for running the operating system 1104. The electronic device 1100 may further include a user identity module (UIM) 1112. The UIM 1112 may be a memory device having a processor built in. The UIM 1112 may include, for example, a subscriber identity module (SIM), a universal integrated circuit card (UICC), a universal subscriber identity module (USIM), a removable user identity module (R-UIM), or any other smart card. The UIM 1112 typically stores information elements related to a mobile subscriber. The UIM 1112 in form of the SIM card is well known in Global System for Mobile (GSM) communication systems, Code Division Multiple Access (CDMA) systems, or with third-generation (3G) wireless communication protocols such as Universal Mobile Telecommunications System (UMTS), CDMA9000, wideband CDMA (WCDMA) and time division-synchronous CDMA (TD-SCDMA), or with fourth-generation (4G) wireless communication protocols such as LTE (Long-Term Evolution).

The electronic device 1100 can support one or more input devices 1120 and/or one or more output devices 1130. Examples of the input devices 1120 may include, but are not limited to, a touch screen/a display screen 1122 (e.g., capable of capturing finger tap inputs, finger gesture inputs, multi-finger tap inputs, multi-finger gesture inputs, or keystroke inputs from a virtual keyboard or keypad), a microphone 1124 (e.g., capable of capturing voice input), a camera module 1126 (e.g., capable of capturing still picture images and/or video images) and/or a physical keyboard 1128. Examples of the output devices 1130 may include, but are not limited to, a speaker 1132 and a display 1134. Other possible output devices can include piezoelectric or other haptic output devices. Some devices can serve more than one input/output function. For example, the touch screen 1122 and the display 1134 can be combined into a single input/output device.

A wireless modem 1140 can be coupled to one or more antennas (not shown in the FIG. 11) and can support two-way communications between the processor 1102 and external devices. The wireless modem 1140 is shown generically and can include, for example, a cellular modem 1142 for communicating at long range with the mobile communication network, a Wi-Fi compatible modem 1144 for communicating at short range with an external Bluetooth-equipped device or a local wireless data network or router, and/or a Bluetooth-compatible modem 1146. The wireless modem 1140 is typically configured for communication with one or more cellular networks, such as a GSM network for data and voice communications within a single cellular network, between cellular networks, or between the electronic device 1100 and a public switched telephone network (PSTN).

The electronic device 1100 can further include one or more input/output ports 1150, a power supply 1152, one or more sensors 1154 for example, an accelerometer, a gyroscope, a compass, a global positioning system sensor (for providing location details) or an infrared proximity sensor for detecting the orientation or motion of the electronic device 1100, a transceiver 1156 (for wirelessly transmitting analog or digital signals) and/or a physical connector 1160, which can be a USB port, IEEE 1294 (FireWire) port, and/or RS-232 port. The illustrated components may not be all-inclusive (e.g., and may be optional), as any of the components shown can be deleted and other components can be added.

The disclosed systems and methods with reference to FIGS. 1 to 11, or one or more operations of the methods 900 and 1000 and the sequence flow diagrams 300 and 400 may be implemented using software including computer-executable instructions stored on one or more computer-readable media (e.g., non-transitory computer-readable media, such as one or more optical media discs), volatile memory components (e.g., DRAM or SRAM), and/or non-volatile memory or storage components (e.g., hard drives or solid-state non-volatile memory components, such as Flash memory components) and executed on a computer (e.g., any suitable computer, such as a laptop computer, net book, Web book, tablet computing device, smart phone, or other mobile computing device).

Such software may be executed, for example, on a single local computer or in a network environment (e.g., via the Internet, a wide-area network, a local-area network, a remote web-based server, a client-server network (such as a cloud computing network), or other such network) using one or more network computers. Additionally, any of the intermediate or final data created and used during implementation of the disclosed methods or systems may also be stored on one or more computer-readable media (e.g., non-transitory computer-readable media) and are considered to be within the scope of the disclosed technology. Furthermore, any of the software-based embodiments may be uploaded, downloaded, or remotely accessed through a suitable communication means.

Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

FIG. 12 is a simplified block diagram of a server system 1200, in accordance with one embodiment of the present disclosure. The server system 1200 is an example of the server system 110 shown and explained with reference to FIG. 1 or the system 200 explained with reference to FIG. 2. The server system 1200 includes a computer system 1205 and one or more databases, such as a database 1210. The computer system 1205 includes a processor 1215 for executing instructions. Instructions may be stored in, for example, but not limited to, a memory 1220. The processor 1215 may include one or more processing units (e.g., in a multi-core configuration). The processor 1215 may be operatively coupled to a communication interface 1225 such that the computer system 1205 is capable of communicating with a remote device such as an electronic device 1235. Example of the electronic device 1235 may include, but is not limited to, the electronic devices 104a to 104c and the adult entertainment device 106 shown in FIG. 1.

The processor 1215 may also be operatively coupled to the database 1210. The database 1210 may be any computer-operated hardware suitable for storing and/or retrieving data. The database 1210 may include multiple storage units such as hard disks and/or solid-state disks in a redundant array of independent disks (RAID) configuration. The database 1210 may include, but is not limited to, a storage area network (SAN) and/or a network attached storage (NAS) system.

In some embodiments, the database 1210 may be integrated within the computer system 1205. For example, the computer system 1205 may include one or more hard disk drives as the database 1210. In other embodiments, the database 1210 is external to the computer system 1205 and may be accessed by the computer system 1205 using a storage interface 1230. The storage interface 1230 is any component capable of providing the processor 1215 with access to the database 1210. The storage interface 1230 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing the processor 1215 with access to the database 1210.

The memory 1220 may be a storage device embodied as one or more volatile memory devices, one or more non-volatile memory devices, and/or a combination of one or more volatile memory devices and non-volatile memory devices, for storing micro-contents information and instructions. The memory 1220 may be embodied as magnetic storage devices (such as hard disk drives, floppy disks, magnetic tapes, etc.), optical magnetic storage devices (e.g., magneto-optical disks), CD-ROM (compact disc read only memory), CD-R (compact disc recordable), CD-R/W (compact disc rewritable), DVD (Digital Versatile Disc), BD (Blu-ray® Disc), and semiconductor memories (such as mask ROM, PROM (programmable ROM), EPROM (erasable PROM), flash ROM, RAM (random access memory), etc.).

FIG. 13 illustrates an exemplary implementation of at least some exemplary embodiments of the exemplary disclosed system, apparatus, and method. As illustrated in FIG. 13, a user's manual editing operation may be a user's click input using a mouse of the exemplary disclosed user interface. For example, a realization of the exemplary disclosed pattern may be created by the mouse by clicking and sliding.

In an embodiment, a computer-implemented method is disclosed. The method includes receiving a media play request initiated from a User Interface (UI) on a user device. The media play request includes a selected media file. The UI includes a plurality of control pattern creation options. The method includes playing the selected multimedia file. The method includes facilitating creation of at least one pattern of a plurality of patterns for the selected media file while accessing the selected multimedia file. The at least one pattern is created by a user using at least one pattern creation option of the plurality of pattern creation options. The method further includes storing the at least one pattern of the selected media file in a corresponding at least one script file of a plurality of script files. The at least one pattern is transformed into corresponding one or more intensity instruction signal sets. The one or more intensity instruction signals are sent to an adult entertainment device communicably connected to the user device to cause customization of sequentially performed at least one predefined act as a series of altering amplitudes of the adult entertainment device in synchronization with the selected multimedia file.

In another embodiment, a system is disclosed. The system includes a communication interface to receive a media play request initiated from a User Interface (UI) on a user device. The media play request includes a selected media file. The UI includes a plurality of control pattern creation options. The system also includes a memory including executable instructions and a processor communicably coupled to the communication interface and configured to execute the instructions, thereby causing the system to access the selected multimedia file. The system is further caused to facilitate creation of at least one pattern of a plurality of patterns for the selected media file while accessing the selected media file. The at least one pattern is created by a user using at least one pattern creation option of the plurality of pattern creation options. The server system is further caused to store the at least one pattern of the selected media file in a corresponding at least one script file of a plurality of script files. The at least one pattern is transformed into corresponding one or more intensity instruction signals. The one or more intensity instruction signals are sent to an adult entertainment device communicably connected to the user device to cause customization of sequentially performed at least one predefined act as series of altering amplitudes of the adult entertainment device in synchronization with the selected multimedia file.

In yet another embodiment, a computer-implemented method is disclosed. The method includes receiving a multimedia selection request initiated from a User Interface (UI) of a media application installed on a user device communicably connected to an adult entertainment device. The multimedia selection request includes a selected multimedia file facilitated by a server system. The method includes detecting at least one script file of a plurality of script files corresponding to the selected media file on the user device and on the server system. The method includes displaying a list of script files detected from the user device or from the server system. The method includes playing the selected media file associated with the selected script file. The method further includes sending one or more intensity instruction signals transformed from the corresponding pattern in the selected script file to the adult entertainment device. The receipt of the one or more intensity signals causes the adult entertainment device to perform customization of sequentially performed at least one predefined act as series of altering amplitudes of the adult entertainment device in synchronization with the selected multimedia file.

Various example embodiments offer, among other benefits, techniques for establishing methods and systems for creating a pattern for a media file. The system may facilitate creation of customized patterns for the media file, thereby providing a flexibility of creating pattern that matches with sexual desire or preference of the user. The system creates the intensity instruction signals that are sent to the adult entertainment device by transforming the created pattern, thereby for example ensuring synchronization of the operation of the adult entertainment device with the media file being played which further enhances the sexual experience of the user.

Although the invention has been described with reference to specific exemplary embodiments, it is noted that various modifications and changes may be made to these embodiments without departing from the broad spirit and scope of the invention. For example, the various operations, blocks, etc. described herein may be enabled and operated using hardware circuitry (for example, complementary metal oxide semiconductor (CMOS) based logic circuitry), firmware, software and/or any combination of hardware, firmware, and/or software (for example, embodied in a machine-readable medium). For example, the apparatuses and methods may be embodied using transistors, logic gates, and electrical circuits (for example, application specific integrated circuit (ASIC) circuitry and/or in Digital Signal Processor (DSP) circuitry).

The present disclosure is described above with reference to block diagrams and flowchart illustrations of method and system embodying the present disclosure. It will be understood that various blocks of the block diagram and flowchart illustrations, and combinations of blocks in the block diagrams and flowchart illustrations, respectively, may be implemented by a set of computer program instructions. These set of instructions may be loaded onto a general-purpose computer, special purpose computer, or other programmable data processing apparatus to cause a device, such that the set of instructions when executed on the computer or other programmable data processing apparatus creates a means for implementing the functions specified in the flowchart block or blocks, although other means for implementing the functions including various combinations of hardware, firmware and software as described herein may also be employed.

Various embodiments described above may be implemented in software, hardware, application logic or a combination of software, hardware and application logic. The software, application logic and/or hardware may reside on at least one memory, at least one processor, an apparatus or, a non-transitory computer program product. In an example embodiment, the application logic, software or an instruction set is maintained on any one of various conventional computer-readable media. In the context of this document, a "computer-readable medium" may be any non-transitory medium or means that can contain, store, communicate, propagate or transport the instructions for use by or in connection with an instruction execution system, apparatus, or device, such as a computer. A computer-readable medium may include a computer-readable storage medium that may be any medium or means that can contain or store the instructions for use by or in connection with an instruction execution system, apparatus, or device, such as a computer.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The embodiments were chosen and described in order to best explain the principles of the present disclosure and its practical application, to thereby enable others skilled in the art to best utilize the present disclosure and various embodiments with various modifications, as are suited to the particular use contemplated. It is understood that various omissions and substitutions of equivalents are contemplated as circumstances may suggest or render expedient, but such are intended to cover the application and/or implementation without departing from the spirit or scope of the claims.

The exemplary disclosed system, apparatus, and method may be used in any suitable application for controlling a device based on accumulation of input parameters. For example, the exemplary disclosed system, apparatus, and method may be used in any suitable application for controlling a device based on accumulation of financial transfers (e.g., virtual currency or a virtual gift) such as tips. The exemplary disclosed system, apparatus, and method may be used in any suitable application for controlling an adult toy. The exemplary disclosed system, apparatus, and method may be used in any suitable telecommunication application for adult entertainment.

In at least some exemplary embodiments, the exemplary disclosed method may be a computer-implemented method for providing multimedia based simulation including receiving, by a processor, a multimedia source file selected from a User Interface (UI) on a user device, providing, by the processor, an interactive region through the UI, accessing, by the processor, the selected multimedia source file, generating, by the processor, at least one interactive result from the interactive region received from the user through the user device, and controlling, by the processor, one or more adult entertainment devices to actuate according to the interactive result. The interactive result may include at least one or more control signals, further facilitating, by the processor, creation of at least one or more control patterns through the interactive region of the user device using the one or more control signals. The exemplary disclosed method may also include integrating, by the processor, the one or more control signals into the multimedia source file, and actuating, by the processor, the one or more adult entertainment device to perform sexual stimulation acts of different amplitudes during the multimedia playback. The exemplary disclosed method may further include facilitating, by the processor, to share, forward, and download the one or more control patterns. The sexual stimulation act may include one or more of vibration, rotation, swing, temperature, expansion, suction, inhalation, and contraction. The multimedia source file may include a video file, an audio file, a text file, an image file, and the like. The interactive region may include one or more of a drag and drop option, a touch panel option, a virtual keys option, and a keyboard keys option. The exemplary disclosed method may further include receiving, by the processor, one or more operations of the user's through the interactive region on the UI, and converting, by the processor, the one or more operations of the user's into corresponding one or more interactive result. The multimedia source file may be a recorded file or a live multimedia source file. The exemplary disclosed method may also include defining tip parameters by the processor, receiving, by the processor, a tip from one or more users, wherein the tip includes virtual currency, providing, by the processor, at least one interactive region, outputting an interactive result according to the at least one interactive region, and controlling, by the processor, one or more adult entertainment devices to actuate according to the interactive result.

In at least some exemplary embodiments, the exemplary disclosed system may include an accessory control module, comprising computer-executable code stored in non-volatile memory, a processor, a device of a human user, and an accessory configured to communicate with the device. The accessory control module, the processor, the device, and the accessory may be configured to receive or obtain multimedia data using the device, create one or more control patterns based on the multimedia data, and drive the accessory using the one or more control patterns. The multimedia data may include at least one selected from the group of text data, sound data, image data, video data, and combinations thereof. The one or more control patterns may include a signal set that drives the accessory to sequentially perform a series of different amplitudes of a predefined act. The predefined act may sexually stimulate the human user. The predefined act of the accessory that sexually stimulates the human user and that includes a motor may be at least one selected from the group of vibration, rotation, swinging, inhalation, temperature variation, expansion, contraction, suction, and combinations thereof. The accessory may be an adult toy sexual stimulation device. Creating the one or more control patterns may include receiving data of an editing operation of the human user of the multimedia data. The editing operation may include at least one selected from the group of the human user's click input of the device, the human user's drag and drop input of the device, the human user's touch input received through a mouse of the device, the human user's touch input received through a touch screen of the device, the human user's touch input received through a keyboard of the device, the human user's touch input received through a virtual keyboard of the device, and combinations thereof. The accessory control module, the processor, the device, and the accessory may be configured to convert the editing operation into a signal of the signal set. The accessory control module, the processor, the device, and the accessory may be configured to integrate the one or more control patterns into the multimedia data and synchronize the one or more control patterns with a playback of the multimedia data. The accessory control module, the processor, the device, and the accessory may be configured to synchronously open and display the one or more control patterns via the device as the multimedia data is reloaded. The accessory control module, the processor, the device, and the accessory may be configured to perform at least one selected from the group of sending, sharing, forwarding, copying, pasting, and combinations thereof via a network through which the accessory control module, the processor, the device, and the accessory communicate. The accessory control module, the processor, the device, and the accessory may be configured to drive the accessory that includes one or more accessories, after downloading the one or more control patterns, to sequentially perform the series of the predefined act, the series of the predefined act including a plurality of predefined acts having different amplitudes based on the one or more control patterns. The accessory control module, the processor, the device, and the accessory may be configured to integrate the one or more control patterns into the multimedia data, which may be played and displayed by the device, and drive the accessory, which may include one or more accessories, to sequentially perform the series of the predefined act with a playback of the multimedia data, the series of the predefined act including a plurality of predefined acts having different amplitudes based on the one or more control patterns. The multimedia data being played and displayed may include at least one selected from the group of recorded multimedia, multimedia broadcast live in real-time, and combinations thereof. The accessory control module, the processor, the device, and the accessory may be configured to associate a tipping signal of the human user with an activation command of the one or more control patterns in advance of driving the accessory, and when the tipping signal is received via the device, activate the activation command to provide a control pattern function to the human user to allow the human user to create the one or more control patterns for actuating the accessory that may be a sexual stimulation device using the multimedia data.

In at least some exemplary embodiments, the exemplary disclosed method may include providing a device of a human user, providing one or more sexual stimulation accessories configured to communicate with the device, receiving or obtaining multimedia data using the device, receiving data of an editing operation of the human user of the multimedia data via the device in real-time, converting the editing operation into one or more signals to drive the one or more sexual stimulation accessories to perform a series of different amplitudes of one or more predefined acts, sending the one or more signals to the one or more sexual stimulation accessories synchronously, and controlling the one or more sexual stimulation accessories based on the one or more signals to perform the series of different amplitudes of the one or more predefined acts in synchronization with a playback of the multimedia data via the device. The multimedia data may include at least one selected from the group of text data, sound data, image data, video data, and combinations thereof. The one or more predefined acts may include at least one selected from the group of vibration, rotation, swinging, inhalation, temperature variation, expansion, contraction, suction, and combinations thereof. The multimedia data may be a video and an intensity of operation of the one or more sexual stimulation accessories may be controlled in synchronization with the playback of the video via the device based on the one or more signals. The editing operation may include at least one selected from the group of the human user's click input of the device, the human user's drag and drop input of the device, the human user's touch input received through a mouse of the device, the human user's touch input received through a touch screen of the device, the human user's touch input received through a keyboard of the device, the human user's touch input received through a virtual keyboard of the device, and combinations thereof. The exemplary disclosed method may also include associating a tipping signal of the human user with a payment provided by the human user via the device, and providing access via the device to the human user for the editing operation when the payment and the tipping signal are transferred via the device. Performing the series of different amplitudes of the one or more predefined acts in synchronization with the playback of the multimedia data via the device may be in a time sequence. Each of the one or more sexual stimulation accessories may include a rotor, a stator having a plurality of windings, and a permanent magnet.

In at least some exemplary embodiments, the exemplary disclosed system may include an accessory control module, comprising computer-executable code stored in non-volatile memory, a processor, a device of a human user, an accessory configured to communicate with the device, and a multimedia application program including at least one selected from the group of an online multimedia player, an online multimedia chat room, and combinations thereof. The accessory control module, the processor, the device, and the accessory may be configured to receive or obtain multimedia data using the device, create one or more control patterns based on the multimedia data, drive the accessory using the one or more control patterns, and play the multimedia data via the multimedia application program and display the multimedia data via the device. The multimedia data may include at least one selected from the group of text data, sound data, image data, video data, and combinations thereof. The one or more control patterns may include a signal set that may drive the accessory to sequentially perform a series of different amplitudes of a predefined act. The predefined act may sexually stimulate the human user.

FIGS. 14-20 illustrate other exemplary embodiments of the exemplary disclosed system, apparatus, and method. In at least some exemplary embodiments, the exemplary disclosed system, apparatus, and method may include a sex toy such as an adult toy (e.g., adult entertainment device 106) and a web camera. The exemplary disclosed system, apparatus, and method may include a viewer or streamer (e.g., a tipper) who views a model based on tip collection. The exemplary disclosed system, apparatus, and method may include tips being provided by a user (e.g., a viewer) so that the user may use the exemplary disclosed system, apparatus, and method to participate in the creation of the exemplary disclosed control pattern.

In at least some exemplary embodiments, the exemplary disclosed system, apparatus, and method may allow for one or more users (e.g., users 102a) to interact with models (e.g., users 102b) from a certain distance (e.g., remotely), for example, by allowing the users to provide financial transfers (e.g., tips) to the models during online video chat sessions. The models may define tipping parameters to perform the exemplary disclosed one or more predefined acts, via an adult toy (e.g., adult entertainment device 106), based on an amount of tips received. The exemplary disclosed adult toy may be Wi-Fi, Bluetooth, ZigBee, NFC, or IrDA (e.g., or any other suitable wireless or short range communication technique) enabled to receive commands directly from the server (e.g., server system 110) via a web browser extension (e.g., via network 108) and/or a website hosting an online video chat session. The adult toy may also connect to an application installed on a device operated by a user (e.g., a model), wherein the application may communicate with the web browser extension to relay commands to the adult toy therefrom. The browser extension and/or website may generate live control links to allow certain users to have a live control of the model's adult toy (e.g., adult entertainment device 102b).

Figure 14:
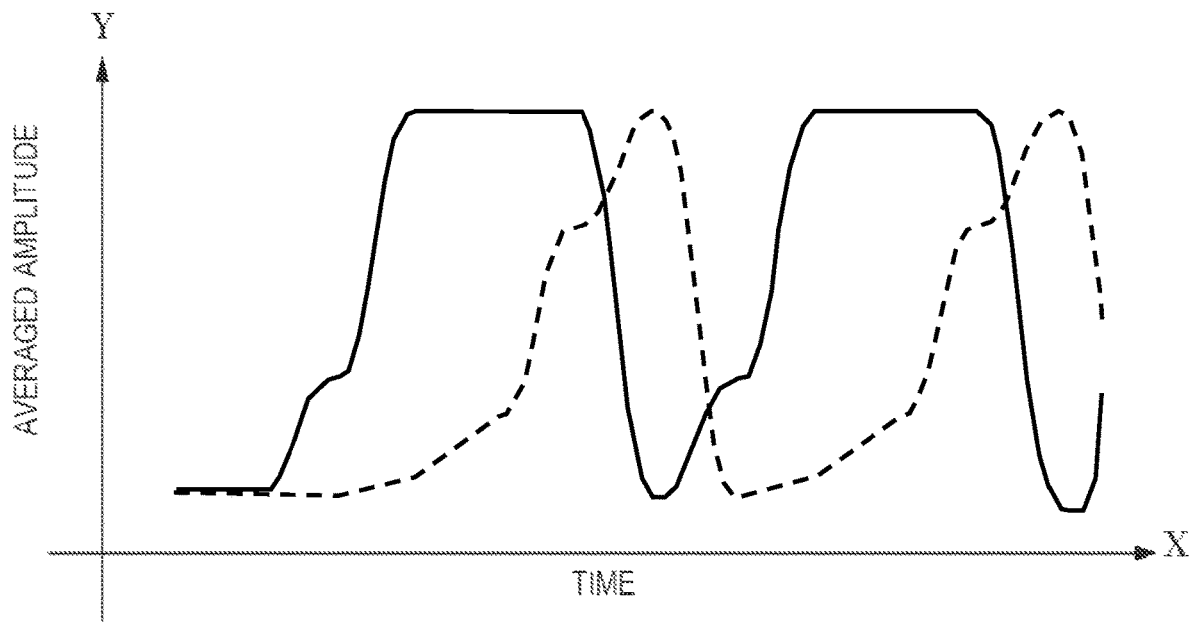
FIG. 14 is a chart illustration, in accordance with an example embodiment of the present disclosure.
Figure 15:
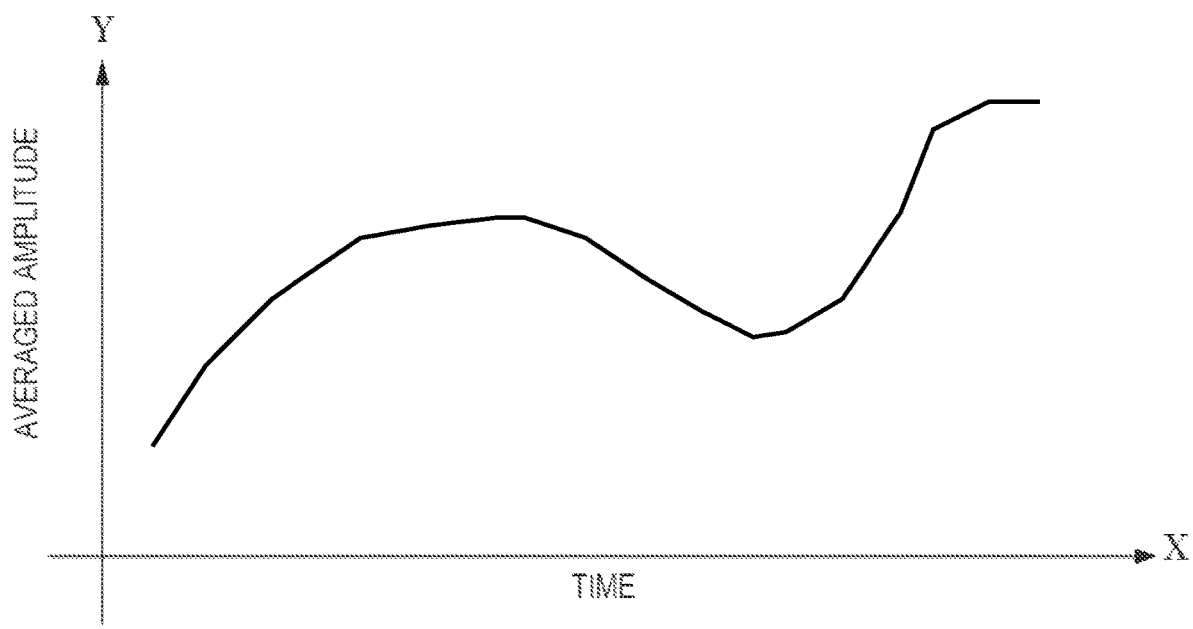
FIG. 15 is a chart illustration, in accordance with an example embodiment of the present disclosure.

FIGS. 14 and 15 illustrate exemplary embodiments of the exemplary disclosed control pattern. The exemplary disclosed control pattern may include one or a plurality of control signals. The at least one instruction signal set may actuate the exemplary disclosed sexual stimulation device (e.g., adult entertainment device 106) to sequentially perform one or more series of predefined acts (e.g., different predefined acts and/or different levels of one or more predefined acts and/or different accessories (e.g., different toys among a set of toys)). One type (e.g., kind) of the predefined act or one level of the predefined act may correspond to one instruction signal. Different instruction signals may together comprise the instruction signal set for example as illustrated in FIG. 14. The instruction signals may be configured to cause customization of the predefined act such as, for example, vibration, rotation, swinging, inhalation, temperature variation, temperature control, stretching, reciprocation, expansion, suction, bending, and/or contraction of the adult toy. Different levels of operation of the exemplary disclosed accessory while performing the predefined act may include different levels of amplitude, frequency, acceleration, temperature, periodicity, and/or duration.

FIGS. 16-19 illustrate exemplary embodiments for creating the exemplary disclosed control pattern. Viewers (e.g., fans such as users 102a) of a user (e.g., a model such as user 102b) may provide financial transfers (e.g., tips) to create the exemplary disclosed control pattern. In at least some exemplary embodiments, a model (e.g., user 102b) may provide settings via user device 104b for users (e.g., users 102a) to create sub-patterns of the control pattern by providing tips, with the sub-patterns forming the exemplary disclosed control pattern.

Figure 16:
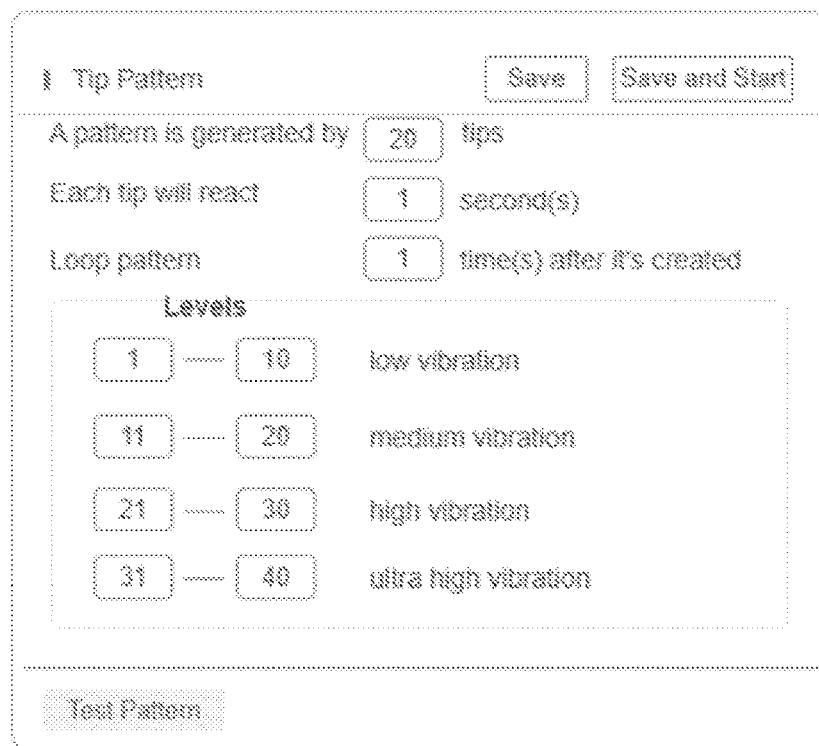
FIG. 16 is an exemplary illustration of a user interface display, in accordance with an example embodiment of the present disclosure.

FIG. 16 illustrates an exemplary display of user device 104a and/user device 104b for configuring tip parameters (e.g., different tip parameters) for creating sub-patterns (e.g., different sub-patterns). For example, a model (e.g., user 102b) may configure tip parameters via user device 104b for example as illustrated in FIG. 16. The exemplary disclosed system may then collect tips from users (e.g., users 102a) via devices 104a. For example, user 102a may provide a tip that may fall into the tip parameters for example as illustrated in FIG. 16 (e.g., or any other desired tip parameters) that may be displayed on user device 104a. Users 102a may create sub-patterns by providing tips based on the tip parameters set by users 102b. For example based on the exemplary tip parameters illustrated in FIG. 16, a tip amount of between 1 and 10 (e.g., of any amount of value or money such as, for example, dollars, bitcoin, and/or virtual currency) may produce a sub-pattern for low vibration, a tip amount of between 11 and 20 may produce a sub-pattern for medium vibration, a tip amount of between 21 and 30 may produce a sub-pattern for high vibration, and a tip amount of between 31 and 40 may produce a sub-pattern for ultra high vibration. The exemplary disclosed tip amounts may also produce sub-patterns having desired predefined acts on desired accessories for any desired amount of time. For example in another exemplary embodiment, a tip amount of between a first tip amount and a second tip amount (e.g., any desired amounts) may produce a sub-pattern for a [first toy having a low vibration for a first time period (e.g., 5 seconds), a tip amount of between a third tip amount and a fourth tip amount may produce a sub-pattern for a second toy having a high rotation for the first time period (e.g., 5 seconds), a tip amount between a fifth tip amount and a sixth tip amount may produce a sub-pattern for a third toy having a medium suction for a second time period (e.g., 10 seconds), a tip amount between a seventh tip amount and an eighth tip amount may produce a sub-pattern for a fourth toy having a an ultra high swinging for a third time period (e.g., 6 seconds), and/or any other desired combinations of toys, levels, predefined acts, and/or time periods.

In at least some exemplary embodiments, smoothing of a performance between adjacent nodes may be performed. For example, a first node (e.g., of a first tipper) may indicate that the operation (e.g., vibration) is medium (e.g., a medium level of vibration), and the second node may indicate that the vibration is ultra high (e.g., an ultra high level of vibration). The toy may be actuated to vibrate from medium to high, and then to ultra high, with a transition buffer or time (e.g., or the toy may transition directly from medium to ultra high). Also for example, the first node may indicate a vibration at the high level, and the second node may indicate a rotation at ultra high (e.g., the toy may be actuated to first vibrate from a high to a medium level, and then to rotate from a medium level to a high level and then to ultra high, with a transition buffer or time).

For example as illustrated in FIG. 16, a user (e.g., model such as user 102b) may configure any desired characteristics of the exemplary disclosed input parameter such as tip parameters. User 102b may set a number of tips for generating a control pattern, a time duration for each tip, a number of times the control pattern may repeat (e.g., a loop pattern), and levels at which the exemplary disclosed accessory (e.g., adult entertainment device 106a and/or 106b) may operate for example as described above. Any suitable criteria (e.g., a preset condition) may be configured for ending a collection of tips such as a total number of tips or tippers, a duration of time for receiving tips, and/or any other suitable criteria. For example, an accumulation of financial transfers such as tips may satisfy the preset condition. For example, an accumulation may satisfy a preset condition, wherein the preset condition may include at least one of the following: a preset receiving quantity of the one or more input parameters (e.g., a total number of tippers who have made a financial transfer), a preset receiving sum of corresponding values of the one or more input parameters (e.g., a total amount of tips received from some or all of the tippers such as an aggregate amount of money, virtual currency, and/or value), or a preset duration of the accumulation (e.g., a time period for receiving tips expires). In response to the accumulation satisfying the preset condition, the exemplary disclosed system may send a control signal to actuate the exemplary disclosed adult toy to perform a series of predefined acts (e.g., predefined or predetermined actions or preset actions), wherein the series of the predefined acts (e.g., predefined sexual stimulation acts) is used to sexually stimulate the user. The predefined acts may include vibration, rotation, suction, expansion, contraction, bending, temperature control, stretching, and/or reciprocation.

Tips may thereby be collected from tippers (e.g., users 102a) via user devices 104a (e.g., using the exemplary disclosed input parameters displayed for example as illustrated in FIG. 16). Users (e.g., tippers such as users 102a) may utilize the exemplary disclosed input parameters (e.g., as illustrated in FIG. 16) to create customized sub-patterns based on their tips (e.g., based on a tip amount of each tip).

Figure 17:
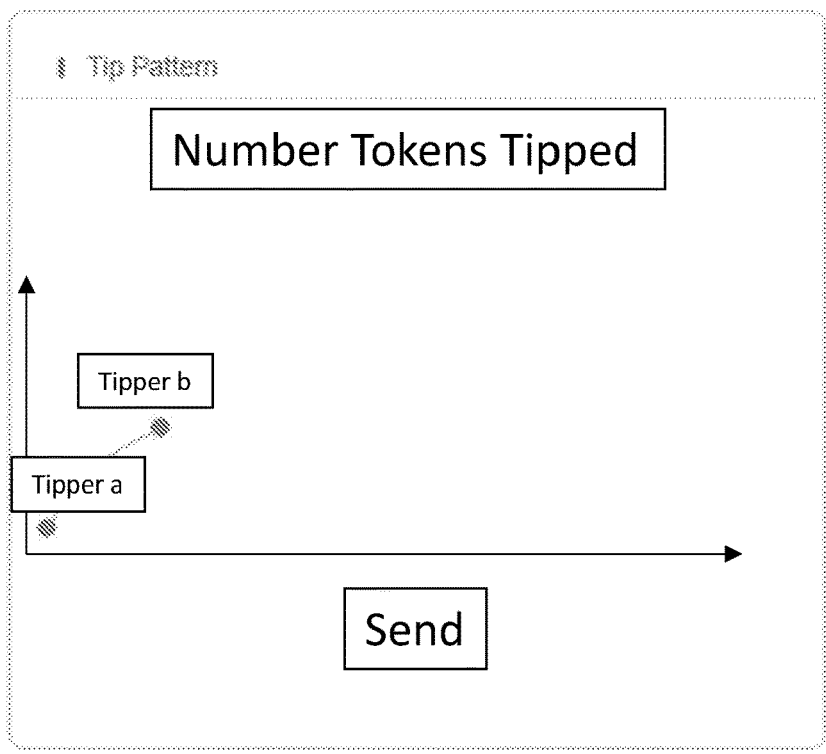
FIG. 17 is an exemplary illustration of a user interface display, in accordance with an example embodiment of the present disclosure.
Figure 18:
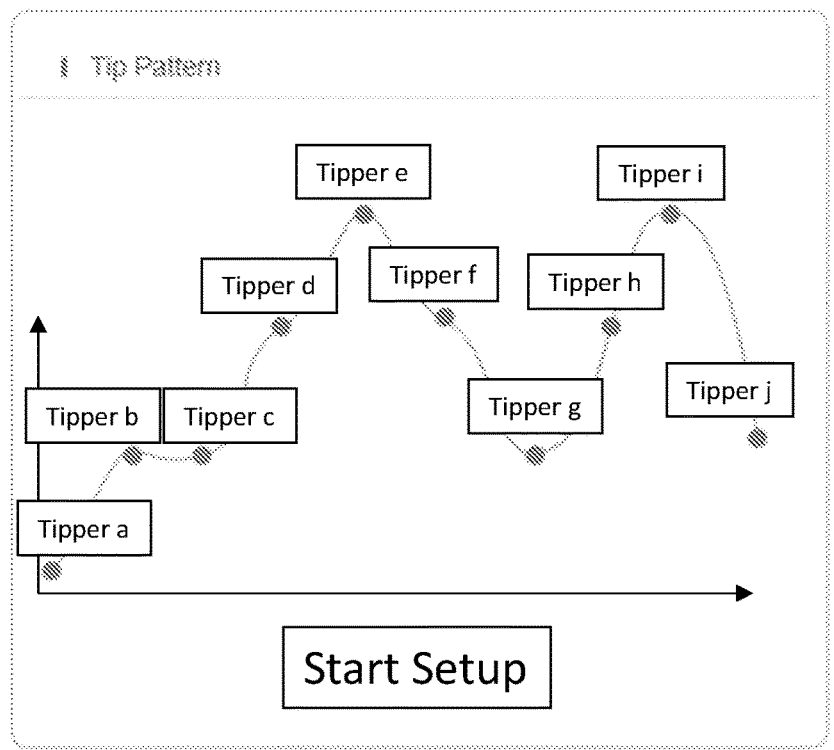
FIG. 18 is an exemplary illustration of a user interface display, in accordance with an example embodiment of the present disclosure.

FIGS. 17 and 18 illustrate an exemplary creation of a control pattern including a plurality of sub-patterns (e.g., Tippers a-j). For example, Tipper "a" may provide a first sub-pattern based on entering input for the input parameter via user device 104, Tipper "b" may provide a second sub-pattern, and so on (e.g., until Tipper "j" provides a tip or any other desired number of tippers provide tips). Sub-patterns may be added based on the order in which tips are provided.

The exemplary disclosed system, apparatus, and method may combine some or all of the created sub-patterns into a control pattern (e.g., a whole or entire control pattern). In at least some exemplary embodiments, the sub-patterns may be combined chronologically (e.g., in an order in which each tipper provides the tip using the input parameters to create the tipper's sub-pattern).

Figure 19:
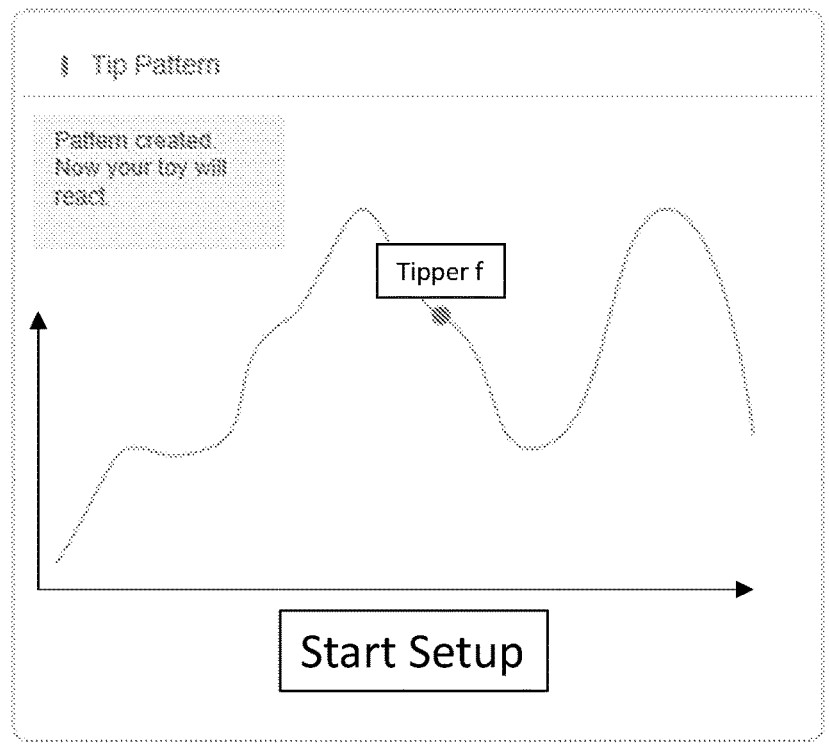
FIG. 19 is an exemplary illustration of a user interface display, in accordance with an example embodiment of the present disclosure.

The completed control pattern may then be used (e.g., played) to control the exemplary disclosed accessory (e.g., adult entertainment device 106). For example as illustrated in FIG. 19, the control pattern may be played to control adult entertainment device 106 to perform the exemplary disclosed predefined act at varying levels (e.g., amplitudes). The control pattern may be repeated as desired (e.g., a finite number of times based on the input parameters for example based on the loop pattern as illustrated in FIG. 16). The exemplary disclosed adult toy may thereby be controlled according to the sub-patterns provided by the tippers (e.g., users 102a) and contained in the exemplary disclosed control pattern. The exemplary disclosed system, apparatus, and method may allow for fans (e.g., users 102a and/or 102b) of a model (e.g., user 102a or user 102b) to provide financial transfers (e.g., send tips) to create sub-patterns of the exemplary disclosed control pattern for controlling the exemplary disclosed adult toy of the model (e.g., and/or adult toys of one or more users such as viewers).

Figure 20:
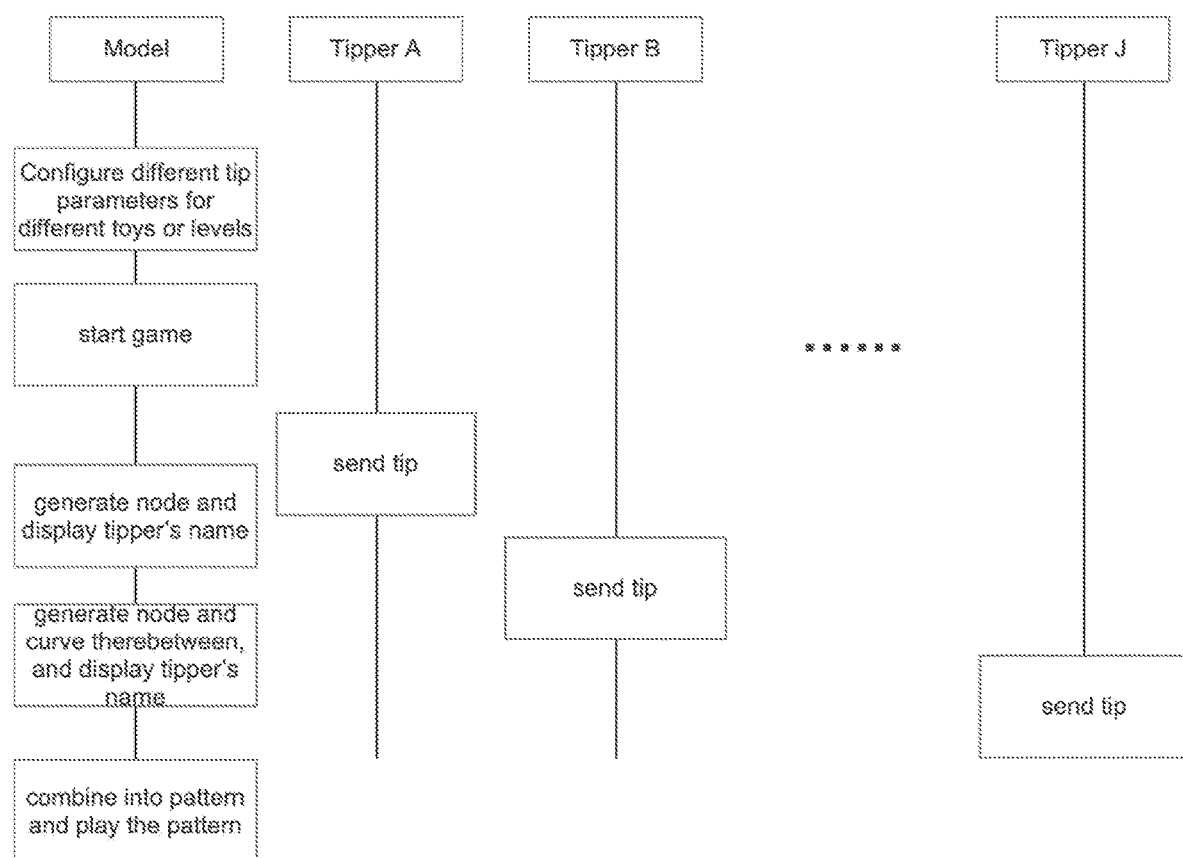
FIG. 20 is an exemplary sequence flow diagram, in accordance with an example embodiment of the present disclosure.

FIG. 20 illustrates an exemplary process of the exemplary disclosed system, apparatus, and method. A user (e.g., a model such as user 102*b*) may configure input parameters. For example, input parameters may be configured so that collecting tips from 10 tippers (e.g., users 102*a*) may generate 10 sub-patterns that may form the exemplary disclosed control pattern. The exemplary disclosed accessory (e.g., adult entertainment device 106) may be a sex toy (e.g., a vibrator or any other desired accessory). The exemplary disclosed parameters may provide for different levels of operation (e.g., different levels of vibration such as low, medium or middle, high, and/or ultra high) and/or any desired duration level or period (e.g., 2 seconds or any other desired amount of seconds or minutes) for each sub-pattern. For example for a given tip, if the parameter of that tip falls between 11 and 20 then the level would be medium, if the parameter falls between 21 and 30 then the level would be high, and/or if the parameter falls between 31 and 40 then the level would be ultra high. When starting the process (e.g., a game for receiving tips), each time the model receives a tip from a tipper, the system may determine if the parameter of that tip falls within a certain range (e.g., for example as described herein). If the tip falls within the certain (e.g., predetermined) range, the exemplary disclosed system and method may generate a new node (e.g., corresponding to a new sub-pattern for the tip based on one or more input parameters) with the user's (e.g., tipper's such as user 102*a*) name. The new node may include any desired data such as, for example, the tipper's name or nickname, the tipper's identity, the tipper's icon, the tipper's comments, a tipping amount, and/or any other desired information. After collecting 10 qualified tips (e.g., or any other desired threshold), a control pattern having 10 nodes may be generated, and the exemplary disclosed toy may vibrate according to the control pattern. A progress of the number of completed nodes may be displayed (e.g., "4/10" nodes completed) via a display of the exemplary disclosed device.

Any desired application (e.g., game, theme, event, or background) may be incorporated into displays of user devices 104*a* and/or 104*b* for collecting tips. For example, a capture the flag game may be used in which fans (e.g., users 102*a*) compete to tip the most to win a prize (e.g., the model such as user 102*b* may set a duration of the game and may customize the prize for the winner). Also for example, a pop the balloon game may be used in which fans (e.g., users 102*a*) compete to fill a virtual balloon until it pops and a toy (e.g., of the model and/or the winner) reacts (e.g., the model such as user 102*b* may customize the toy reaction, balloon "capacity," and/or deflation settings). Further for example, a jar game may be used in which fans (e.g., users 102*a*) compete or work together to fill a "tip jar" until a goal is reached and the jar tips over so that a toy (e.g., of the model and/or the winner or winners) reacts as the jar is being emptied (e.g., the model such as user 102*b* may set a hidden lucky number that may tip the jar and may provide users with a chance to win). Additionally for example, a progress bar may be used that displays progress for reaching a tip goal in which received tips are shown as progress via the bar (e.g., the model such as user 102*b* may customize how a toy of the model and/or tippers may react when one or more goals is reached).

In at least some exemplary embodiments, the exemplary disclosed system, apparatus, and method may help users such as models (e.g., user 102*b*) to further entertain and incentivize tippers (e.g., users 102*a* such as viewers) so that the tippers may provide an increased amount of financial transfers (e.g., tips) to the model. The exemplary disclosed system, apparatus, and method may thereby help to maintain and increase a revenue or income stream (e.g., tips) to a model.

In at least some exemplary embodiments, the exemplary disclosed system, apparatus, and method may, in response to an accumulation (e.g., of tips) satisfying a preset condition, send a control signal to actuate the exemplary disclosed adult toy to perform a series of predefined acts (e.g., predefined or predetermined actions or preset actions) to sexually stimulate the user. In addition to performing one or more predefined acts according to the exemplary disclosed control pattern, the exemplary disclosed system, apparatus, and method may perform one or more predefined acts in response to multiple users' instructions (e.g., group control), may control the model's toy and viewer's toy to vibrate simultaneously, and/or may allow the model to control the viewer's toy (e.g., allow user 102*b* to view an adult toy of user 102*a*).

In at least some exemplary embodiments, the exemplary disclosed system may include an accessory control module, comprising computer-executable code stored in non-volatile memory, a memory for storing instructions and a processor for executing the instructions, a user device of a user, and an accessory configured to communicate with the user device. The accessory control module, the memory and the processor, the user device, and the accessory may be configured to accumulate receipt of one or more input parameters, determine whether an accumulation satisfies a preset condition, wherein the preset condition includes at least one of a preset receiving quantity of the one or more input parameters, a preset receiving sum of values of the one or more input parameters, or a preset time duration of the accumulation, and in response to the accumulation satisfying the preset condition, send a control signal to actuate the accessory to perform a series of predefined acts, wherein the series of predefined acts is configured to sexually stimulate the user. Accumulating receipt of the one or more input parameters may include at least one of, in response to receiving one of the one or more input parameters, generating a control sub-pattern corresponding to each of the one or more input parameters chronologically with different control sub-patterns indicating actuating different accessories, actuating the accessory to perform different predefined acts, or actuating the accessory to perform different levels of the series of predefined acts. Generating the control sub-pattern corresponding to each of the one or more input parameters may include at least one of pre-configuring different control sub-patterns according to different values of the one or more input parameters or different ranges into which the one or more input parameters fall, or randomly selecting one control sub-pattern from all control sub-patterns. The series of predefined acts of the accessory that sexually stimulates the user may include at least one selected from the group of vibration, rotation, suction, expansion, contraction, bending, temperature control, stretching, reciprocation, and combinations thereof. The different levels of the series of predefined acts may include at least one selected from the group of amplitude, frequency, acceleration, temperature, periodicity, and duration, and combinations thereof. Sending the control signal to actuate the accessory to perform the series of predefined acts may include combining the generated control sub-patterns into a control pattern, wherein the generated control sub-patterns correspond to the series of predefined acts, and converting the control pattern into the control signal. Generating control sub-patterns corresponding to the one or more input parameters chronologically may include first providing a user interface of the user device, next, in response to receiving each one of the one or more input parameters, generating a node associated with each one of the one or more input parameters on the user interface, wherein a horizontal axis position of each generated node is proportional to a receiving time of each one of the one or more input parameters, and a vertical axis position of each generated node is proportional to the levels of the predefined acts indicated by the control sub-patterns corresponding to each one of the one or more input parameters, and then drawing a smooth curve between each newly generated node and a predecessor thereof. Each generated node may be marked with node information including at least one selected from the group of user information of who sent input parameter data associated with the generated node, identification of an adult toy type of the accessory, predefined act identification, and combinations thereof. Generating control sub-patterns corresponding to the one or more input parameters chronologically may further include at least one of prompting the user via the user device of the generation of each newly generated node or a progress of completing a generation of all nodes. Sending the control signal to actuate the accessory to perform the series predefined acts may further include completing a generation of all nodes and the drawing of the smooth curves, and playing the control pattern via the user device to control the accessory. Playing the control pattern may include displaying, via the user interface, a guide object that moves along the drawn smooth curves according to a preset play speed and a preset number of cycles, when the guide object reaches each node, displaying the node information of the corresponding node, and actuating the accessory to perform the series of predefined acts according to the preset play speed and the preset number of cycles of the control pattern. Playing the control pattern may further include if a difference between the levels of predefined acts corresponding to two adjacent nodes exceeds a preset value, smoothing a performance between the two corresponding predefined acts. The one or more input parameters may be virtual currency or a virtual gift sent by at least one of the user or one or more other users. The one or more input parameters may be a plurality of input parameters, and accumulating the receipt of the plurality of input parameters may further include in response to receiving one of the plurality of the input parameters, determining whether the one of the plurality of the input parameter falls within a preset threshold, and if the one of the plurality of the input parameters falls within the preset threshold, generating a control sub-signal to actuate the accessory to perform one of the series of predefined acts indicated by a control sub-pattern corresponding to the one of the plurality of input parameters. Determining whether the accumulation satisfies the preset condition may include providing a game application on a user interface of the user device, in response to accumulating the receipt of the one or more input parameters, updating a completed progress of the game application, and determining that the accumulation satisfies the preset condition based on the completed progress of the game application.

In at least some exemplary embodiments, the exemplary disclosed method may include providing a user device of a human user, providing an adult toy configured to communicate with the user device, accumulating receipt of a plurality of input parameters via the user device, determining whether an accumulation satisfies a preset condition, wherein the preset condition includes at least one of a preset receiving quantity of the plurality of input parameters, a preset receiving sum of values of the plurality of input parameters, or a preset time duration of the accumulation, and in response to the accumulation satisfying the preset condition, sending a control signal to actuate the adult toy to perform a series of predefined acts, wherein the series of predefined acts is configured to sexually stimulate the human user. Accumulating receipt of the plurality of input parameters may include at least one of, in response to receiving one of the plurality of input parameters, generating a control sub-pattern corresponding to each of the plurality of input parameters chronologically with different control sub-patterns indicating actuating different adult toys, actuating the adult toy to perform different predefined acts, or actuating the adult toy to perform different levels of the series of predefined acts. The series of predefined acts of the adult toy that sexually stimulates the human user may include at least one selected from the group of vibration, rotation, suction, expansion, contraction, bending, temperature control, stretching, reciprocation, and combinations thereof. Sending the control signal to actuate the adult toy to perform the series of predefined acts may include combining the generated control sub-patterns into a control pattern, wherein each of the generated control sub-patterns corresponds to each of the series of predefined acts, and converting the control pattern into the control signal.

In at least some exemplary embodiments, the exemplary disclosed system may include an accessory control module, comprising computer-executable code stored in non-volatile memory, a memory for storing instructions and a processor for executing the instructions, a user device of a human user, and a sexual stimulation device configured to communicate with the user device. The accessory control module, the memory and the processor, the user device, and the sexual stimulation device may be configured to accumulate receipt of a plurality of input parameters, determine whether an accumulation satisfies a preset condition, wherein the preset condition includes at least one of a preset receiving quantity of the plurality of input parameters, a preset receiving sum of values of the plurality of input parameters, or a preset time duration of the accumulation, and in response to the accumulation satisfying the preset condition, send a control signal to actuate the sexual stimulation device to perform a series of predefined acts, wherein the series of predefined acts is configured to sexually stimulate the human user. The plurality of input parameters may include at least one selected from the group of virtual currency, a virtual gift sent by at least one of the human user or one or more other human users, and combinations thereof.

The exemplary disclosed system, apparatus, and method may provide an efficient and effective technique for controlling devices such as adult toys based on accumulation of input. For example, the exemplary disclosed system, apparatus, and method may provide for control of devices such as adult toys based on accumulation of financial transfers such as tips. The exemplary disclosed system, apparatus, and method may provide an efficient and effective technique for controlling devices to perform predefined acts at desired amplitudes and/or patterns based on accumulation of input parameters. The exemplary disclosed system, apparatus, and method may increase viewer involvement with tipping activity and may increase effectiveness of visualization of the system when viewers tip. The exemplary disclosed system, apparatus, and method may encourage tipping and may increase interaction between models and viewers during broadcast streaming.

In at least some exemplary embodiments, the exemplary disclosed system, apparatus, and method may utilize sophisticated machine learning and/or artificial intelligence techniques to prepare and submit datasets and variables to cloud computing clusters and/or other analytical tools (e.g., predictive analytical tools) which may analyze such data using artificial intelligence neural networks. The exemplary disclosed system may for example include cloud computing clusters performing predictive analysis. For example, the exemplary neural network may include a plurality of input nodes that may be interconnected and/or networked with a plurality of additional and/or other processing nodes to determine a predicted result. Exemplary artificial intelligence processes may include filtering and processing datasets, processing to simplify datasets by statistically eliminating irrelevant, invariant or superfluous variables or creating new variables which are an amalgamation of a set of underlying variables, and/or processing for splitting datasets into train, test and validate datasets using at least a stratified sampling technique. The exemplary disclosed system may utilize prediction algorithms and approach that may include regression models, tree-based approaches, logistic regression, Bayesian methods, deep-learning and neural networks both as a stand-alone and on an ensemble basis, and final prediction may be based on the model/structure which delivers the highest degree of accuracy and stability as judged by implementation against the test and validate datasets.

It will be appreciated that computer program instructions may include computer executable code. A variety of languages for expressing computer program instructions are possible, including without limitation C, C++, Java, JavaScript, assembly language, Lisp, HTML, Perl, and so on. Such languages may include assembly languages, hardware description languages, database programming languages, functional programming languages, imperative programming languages, and so on. In some embodiments, computer program instructions can be stored, compiled, or interpreted to run on a computing device, a programmable data processing apparatus, a heterogeneous combination of processors or processor architectures, and so on. Without limitation, embodiments of the system as described herein can take the form of web-based computer software, which includes client/server software, software-as-a-service, peer-to-peer software, or the like.

In some embodiments, a computing device enables execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more threads. The thread can spawn other threads, which can themselves have assigned priorities associated with them. In some embodiments, a computing device can process these threads based on priority or any other order based on instructions provided in the program code.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

It will be apparent to those skilled in the art that various modifications and variations can be made to the disclosed system and method. Other embodiments will be apparent to those skilled in the art from consideration of the specification and practice of the disclosed method and apparatus. It is intended that the specification and examples be considered as exemplary only, with a true scope being indicated by the following claims.

What is claimed is:

1. A method, comprising:
   establishing communication between a user device operable by a human user and an adult toy;
   accumulating a plurality of input parameters received via the user device; and
   in response to a preset condition being satisfied during the accumulating, stopping the accumulating and sending a control signal to actuate the adult toy to perform a series of predefined acts, wherein the series of predefined acts comprise acts for sexually stimulating the human user,
   wherein:
   the sending the control signal includes (i) combining plural control sub-patterns into a control pattern, each of the plural control sub-patterns corresponding to a respective one of the plurality of input parameters, and the plural control sub-patterns respectively corresponding to the series of predefined acts, (ii) converting the control pattern into the control signal, and (iii) playing the control pattern to actuate the adult toy to perform the series of predefined acts,
   the accumulating the plurality of input parameters includes generating and displaying a node associated with a respective one of the plurality of input parameters on a user interface of the user device, in response to receipt of each one of the plurality of input parameters,
   a horizontal axis position of each node is proportional to a receiving time of its respective one of the plurality of input parameters,
   a height of each node represents an amplitude indicating an amount by which the one of the plural control sub-patterns associated therewith actuates the adult toy, and
   a width of each node represents a duration during which the one of the plural control sub-patterns associated therewith actuates the adult toy.

2. The method of claim 1, wherein the accumulating comprises, in response to receiving the plurality of input parameters, generating the plural control sub-patterns, and wherein different control sub-patterns among the plural control sub-patterns include control sub-patterns for actuating different accessories, actuating accessories among the different accessories to perform different predefined acts, or actuating the adult toy to perform different levels of the series of predefined acts.

3. The method of claim 2, wherein the generating the plural control sub-patterns includes at least one of fil preconfiguring the different control sub-patterns according to different values of the plurality of input parameters, and (ii) randomly selecting one control sub-pattern from all control sub-patterns.

4. The method of claim 2, wherein the different levels of the series of predefined acts includes levels of at least one of amplitude, frequency, acceleration, temperature, periodicity, and duration.

5. The method of claim 1, wherein a vertical axis position of each node is proportional to different levels of the series of predefined acts indicated by the plural control sub-patterns.

6. The method of claim 2, wherein the generating the plural control sub-patterns includes at least one of:

informing the human user via the user device of the generation of each node associated with a respective one of the plurality of input parameters; and indicating a progress of completing generation of all nodes.

7. The method of claim 1, wherein the playing the control pattern includes:

indicating a progress of playing the control pattern;

displaying, via the user interface, a guide object that moves along the generated nodes according to a preset play speed and a preset number of cycles; and actuating the adult toy to perform the series of predefined acts according to the preset play speed and the preset number of cycles of the control pattern.

8. The method of claim 1, wherein the playing the control pattern includes:

when a difference between different levels of the series of predefined acts at adjacent nodes exceeds a preset value, smoothing a performance between the predefined acts at the adjacent nodes.

9. The method of claim 1, wherein the accumulating the plurality of input parameters further includes:

in response to receiving one of the plurality of the input parameters, determining whether the one of the plurality of the input parameters satisfies the preset condition, and in response to determining that the one of the plurality of the input parameters satisfies the preset condition, generating a control sub-signal to actuate the adult toy to perform one of the series of predefined acts indicated by a control sub-pattern corresponding to the one of the plurality of input parameters.

10. The method of claim 1, further including:

providing an application on the user interface of the user device; and in response to accumulating the plurality of input parameters, updating a completed progress of the application.

11. The method of claim 1, wherein satisfying the preset condition includes receiving a saving input via the user device.

12. A system, comprising:

a memory device having stored thereon a set of instructions; and a processor configured to execute said set of instructions to perform processes comprising:

establishing communication between a user device operable by a human user and an adult toy;

accumulating a plurality of input parameters received via the user device; and in response to a preset condition being satisfied during the accumulating, stopping the accumulating and sending a control signal to actuate the adult toy to perform a series of predefined acts, wherein the series of predefined acts comprise acts for sexually stimulating the human user, wherein:

the plurality of input parameters include at least one input parameter selected by a user input operation, the sending the control signal includes (i) combining plural control sub-patterns into a control pattern, each of the plural control sub-patterns corresponding to a chronological time at which a corresponding one of the plurality of input parameters is received, and the plural control sub-patterns respectively corresponding to the series of predefined acts, (ii) converting the control pattern into the control signal, and (iii) playing the control pattern to actuate the adult toy to perform the series of predefined acts, the accumulating the plurality of input parameters includes generating and displaying a node associated with a respective one of the plurality of input parameters on a user interface of the user device, in response to receipt of each one of the plurality of input parameters, a horizontal axis position of each node is proportional to a receiving time of its respective one of the plurality of input parameters, a height of each node represents an amplitude indicating an amount by which the one of the plural control sub-patterns associated therewith actuates the adult toy, and a width of each node represents a duration during which the one of the plural control sub-patterns associated therewith actuates the adult toy.

13. The system of claim 12, wherein the playing the control pattern includes:

indicating a progress of playing the control pattern;

displaying, via the user interface, a guide object that moves along the generated nodes according to a preset play speed and a preset number of cycles; and actuating the adult toy to perform the series of predefined acts according to the preset play speed and the preset number of cycles of the control pattern.

14. The system of claim 12, wherein satisfying the preset condition includes receiving a saving input via the user device.

15. A non-transitory computer-readable storage medium having a program stored thereon, the program being executable by a computer to control the computer to control processes comprising:

establishing communication between a user device operable by a human user and an adult toy;

accumulating a plurality of input parameters received via the user device; and in response to a preset condition being satisfied during the accumulating, stopping the accumulating and sending a control signal to actuate the adult toy to perform a series of predefined acts, wherein the series of predefined acts comprise acts for sexually stimulating the human user, wherein:

the plurality of input parameters include at least one input parameter selected by a user input operation, the sending the control signal includes (i) combining plural control sub-patterns into a control pattern, each of the plural control sub-patterns corresponding to a chronological time at which a corresponding one of the plurality of input parameters is received, and the plural control sub-patterns respectively corresponding to the series of predefined acts, (ii) converting the control pattern into the control signal, and (iii) playing the control pattern to actuate the adult toy to perform the series of predefined acts, the accumulating the plurality of input parameters includes generating and displaying a node associated with a respective one of the plurality of input parameters on a user interface of the user device, in response to receipt of each one of the plurality of input parameters, a horizontal axis position of each node is proportional to a receiving time of its respective one of the plurality of input parameters, and a height of each node represents an amplitude indicating an amount by which the one of the plural control sub-patterns associated therewith actuates the adult toy.

16. The non-transitory computer-readable storage medium of claim 15, wherein an arbitrary one of the plural control sub-patterns is alterable by modifying the input parameter corresponding thereto, and actuation of the adult toy during one of the series of predefined acts corresponds to the arbitrary one of the plural control sub-patterns being performed according to a modification thereto.

* * * * *